(12) United States Patent
Kralik et al.

(10) Patent No.: US 7,463,357 B2
(45) Date of Patent: Dec. 9, 2008

(54) WIDE DYNAMIC RANGE CHEMICAL ARRAY READER

(75) Inventors: John C. Kralik, Devon, PA (US); Tariq N. Faiz, Hockessin, DE (US)

(73) Assignee: Agilent Technologies, Inc., Santa Clara, CA (US)

( * ) Notice: Subject to any disclaimer, the term of this patent is extended or adjusted under 35 U.S.C. 154(b) by 178 days.

(21) Appl. No.: 11/290,100

(22) Filed: Nov. 29, 2005

(65) Prior Publication Data

US 2007/0121110 A1    May 31, 2007

(51) Int. Cl.
*G01J 3/30* (2006.01)
(52) U.S. Cl. ..................... 356/417; 356/318
(58) Field of Classification Search ............... 356/318, 356/417; 250/226, 207, 208.1
See application file for complete search history.

(56) References Cited

U.S. PATENT DOCUMENTS 4,070,112 A * 1/1978 Tsunazawa et al. ......... 356/319
6,141,096 A * 10/2000 Stern et al. .................. 356/318
6,518,556 B2   2/2003 Staton et al.
6,806,460 B2 * 10/2004 Corson ....................... 250/226
2002/0031737 A1 * 3/2002 Von Drasek et al. ......... 431/79
2004/0239922 A1  12/2004 Modlin et al.
2005/0057676 A1   3/2005 Weiner et al.
2005/0061990 A1 * 3/2005 Curry et al. ............... 250/459.1
2005/0079102 A1   4/2005 Staton et al.
2005/0079603 A1   4/2005 Sandstrom
2005/0243321 A1 * 11/2005 Cohen et al. ................ 356/432

OTHER PUBLICATIONS

Agilent G2565AA and Agilent G2565BA Microarray Scanner System with SureScan Technology, User Manuel (v.6.3) Fifth Edition, Dec. 2003.

* cited by examiner

*Primary Examiner*—Kara E. Geisel
*Assistant Examiner*—Abdullahi Nur

(57) ABSTRACT

A system for detecting a predetermined wavelength of light emitted from an area on the surface of a chemical array is provided. Aspects of the system include: a beam splitter for splitting emitted light into two or more light beams and a detector for detecting photons in each of the two produced light beams. Methods of detecting light using the subject system, programming for performing the subject methods and an array reader containing the subject system are also provided.

35 Claims, 9 Drawing Sheets

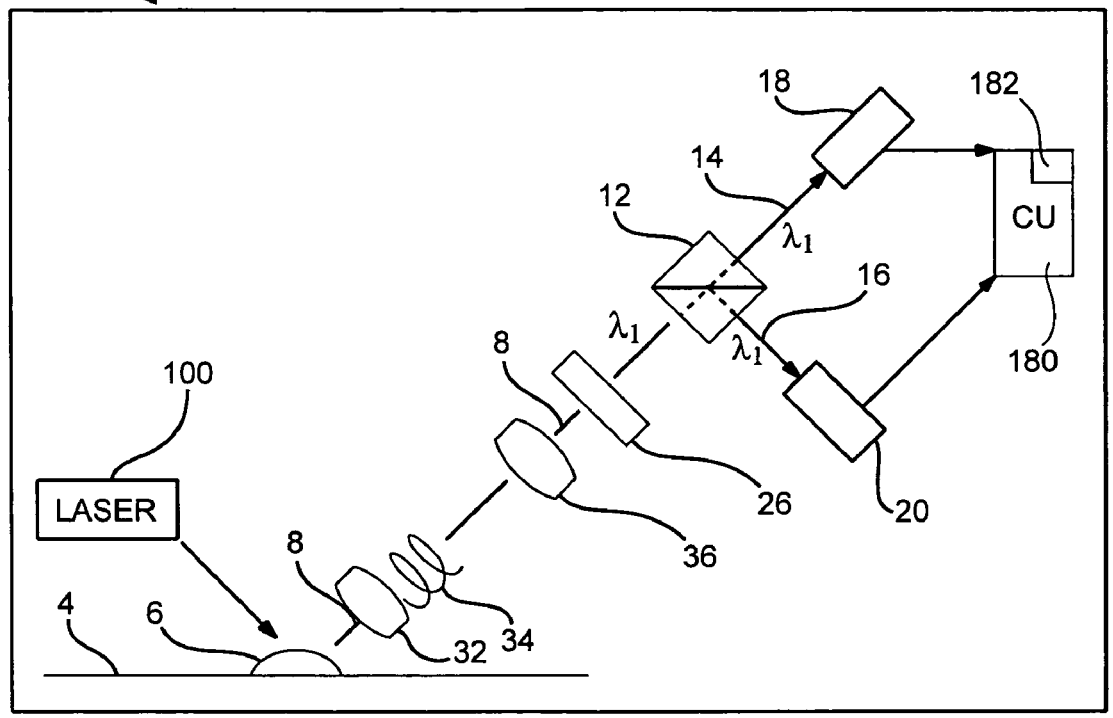

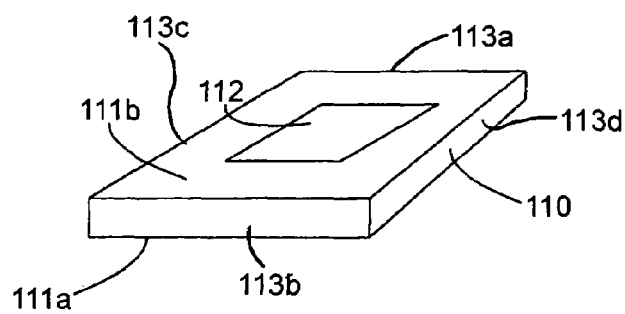
FIG. 9
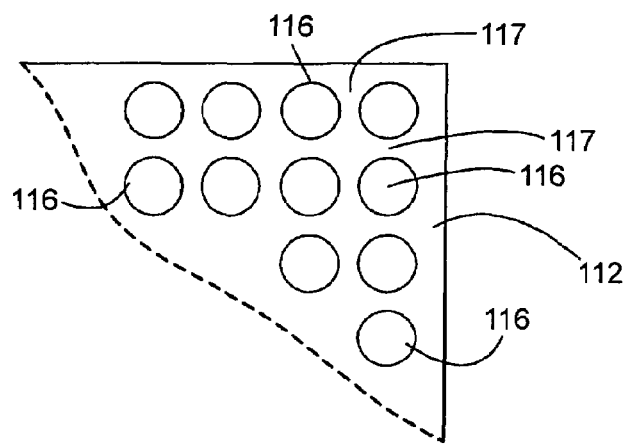
FIG. 10
FIG. 11
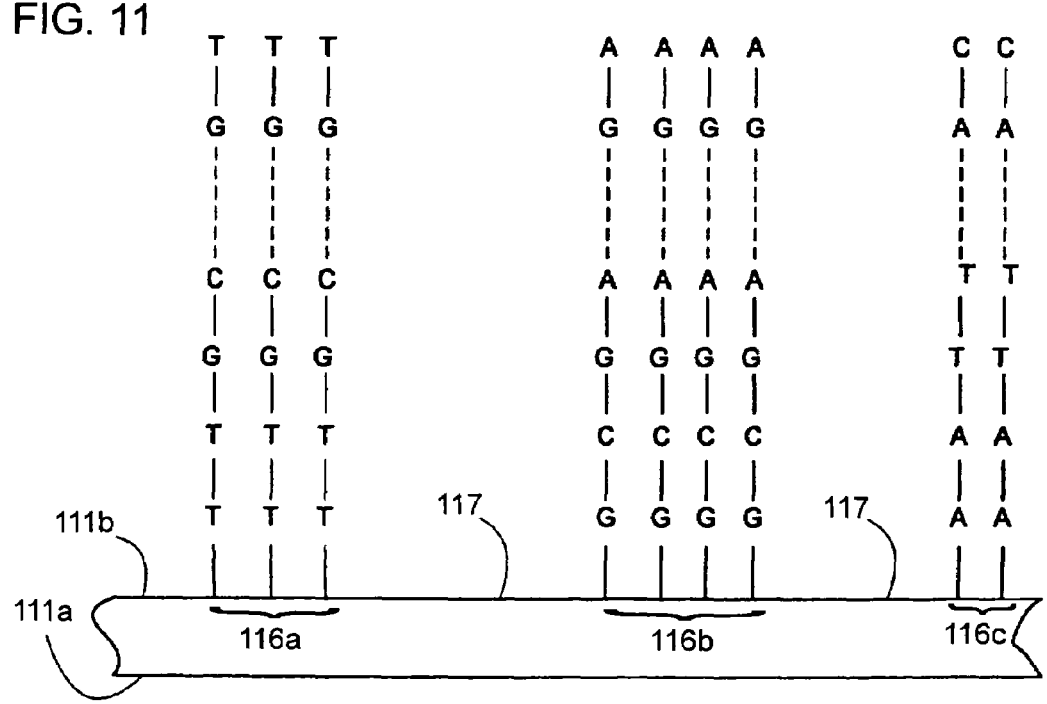

WIDE DYNAMIC RANGE CHEMICAL ARRAY READER

BACKGROUND

Arrays of surface-bound binding agents, known in the art as chemical arrays, may be used to detect the presence of particular targets, e.g., biopolymers, in solution. The surface-bound probes may be oligonucleotides, peptides, polypeptides, proteins, antibodies or other molecules capable of binding with target molecules in solution. Such binding interactions are the basis for many of the methods and devices used in a variety of different fields, e.g., genomics (in sequencing by hybridization, SNP detection, differential gene expression analysis, identification of novel genes, gene mapping, finger printing, etc.), CGH, location analysis and proteomics.

One typical array assay method involves biopolymeric probes immobilized in an array on a substrate, such as a glass substrate or the like. A fluid containing sample is placed in contact with the array substrate, covered with another substrate such as a coverslip or the like to form an assay area and placed in an environmentally controlled chamber such as an incubator or the like. Usually, the targets in the sample bind to the complementary probes on the substrate to form a binding complex. The pattern of binding by target molecules to biopolymer probe features or spots on the substrate produces a pattern on the surface of the substrate and provides desired information about the sample. In certain instances, the target molecules are labeled with a detectable tag such as a fluorescent tag or chemiluminescent tag. The resultant binding interaction or complexes of binding pairs are then detected and read or interrogated, for example by optical means, although other methods may also be used. For example, laser light may be used to excite fluorescent tags, generating a signal only in those spots on the biochip that have a target molecule and thus a fluorescent tag bound to a probe molecule. This pattern may then be digitally scanned for computer analysis.

For each pixel of a scan, a light detector (e.g., a photomultiplier tube) typically detects light emitted from the surface of a microarray, and outputs an analog signal that changes in amplitude according to the amount of emitted light entering the detector. This analog signal is usually sampled and digitized using an analog-to-digital converter (A/D converter) and integrated using a signal processor (e.g., a DSP) to provide data, e.g., a numerical evaluation of the brightness of the pixel. This data is usually stored and analyzed at a later date.

Current detection methodologies, however, are limited because the range of light intensity emitted by an array generally exceeds the linear dynamic range of the photodetection systems used for the detection of that light. Accordingly, in scanning an array, typical photodetection systems produce a significant number of data points that are either saturated (i.e., at or above the maximum of the linear dynamic range of the detector), or indistinguishable from background (i.e., at or below the minimum of the dynamic range of the detector).

While the gain of photodetection system may be adjusted (i.e., increased or decreased) in an attempt to maximize both signal strength and detection, such adjustments often have little effect on the overall quality of the data produced by the photodetection system because decreasing the gain of a detection system decreases the sensitivity of the system (i.e., decreases its ability to detect low magnitude signals). On the other hand, increasing the gain of the detection system often causes saturation of high intensity signals. In addition, consecutive scans at different detection gain increases the time per scan, and leads to photobleaching of the fluorescent dyes used in typical array experiments.

SUMMARY

Embodiments include a wide dynamic range system for detecting light emitted from an area on the surface of a chemical array. Aspects of the system include (a) a beam splitter that is configured for splitting the light emitted into a first and a second light beam, (b) a first detector for detecting photons in the first light beam, and (c) a second detector for detecting photons in the second light beam. In certain embodiments, the system may include a processing system for integrating and outputting numerical information representing the light signal detected by the first and second detectors. Also provided are methods of detecting light using the subject system, programming for performing the subject methods and an array reader containing the subject system. A kit for retrofitting an array reader is also provided. The subject invention finds use in a variety of different applications, including genomics, proteomics, and bioinformatics applications.

In certain embodiments the first and second detectors may be the same type of detector. In such embodiments, the first detector may be set at a different gain (i.e., a higher or lower gain) than the second detector. In alternative embodiments, the first and second detectors may be of different types, wherein a first detector may be configured to detect high intensity light and the second detector may be configured to detect light at a lower intensity than the first. The first and second detector may be of different sensitivities, for instance, the first detector may be more sensitive than the second detector (i.e., the first detector is able to detect light at a lower intensity than the second detector), in which case the most sensitive detector may be set at a higher gain than the less sensitive detector. The first and second detectors may be any type of detector capable of detecting a light emitted from an area of a surface. In representative embodiments, they have, or are configured to have, an overlapping dynamic range. For instance, the first and/or second detectors may be a photo multiplier tube (PMT), a photodiode, an avalanche photodiode (APD), a charge coupled device (CCD), a charge-injection device (CID), a complimentary-metal-oxide-semiconductor detector device (CMOS), a silicon photo-diode, and the like.

In certain embodiments, the subject multi-detector system may further include a collimating lens, an optical fiber (e.g., a multi-mode optical fiber), a filter, and/or the like. For instance, in one embodiment, a system is provided for detecting light (e.g., of a predetermined wavelength) emitted from an area on a surface of a chemical array that includes a filter, a collimating lens, a beam splitter configured to split light into a first and second light beam each having the pre-determined wavelength of light, a first detector for detecting photons in the first light beam, and a second detector for detecting photons in the second light beam of predetermined wavelength.

Embodiments of the invention also provide an array reader (e.g., a scanner) including a laser excitation system, and subject multi-detector system, as described above. In certain embodiments, the array reader produces data for an array, and can contain a data processing system and/or a storage medium (e.g., computer memory) for storing processed data.

Additionally, aspects of the invention provide methods that include: contacting a sample with a chemical array (e.g., for instance an array of biopolymers such as polynucleotides or polypeptides) of two or more chemical ligands immobilized on a surface of a solid support; and reading the array with the array reader described above to obtain data and/or storing the data on a computer-readable medium such as a computer memory.

The invention also provides a method for detecting light emitted from an area on a surface of a chemical array. In general, the method includes splitting the emitted light into a first and a second light beam, each containing the pre-determined wavelength of light, detecting photons in the first light beam with a first detector, and detecting photons in the second light beam with a second detector. The method may also include collimating and/or filtering the light prior to and/or after splitting it. Additionally, the method may involve processing the detected photons in the first and second detectors to produce data and, in certain embodiments storing the data.

The invention also provides a computer-readable medium that contains programming for execution by a data processing system of an array reader, the programming including: instructions for analyzing signals produced by the first and second detectors of a dual detector detection system, as described above, to produce data; instructions for storing the data produced on a computer readable medium; and instructions for outputting the data.

In any of the above embodiments, the array may be any kind of chemical array, e.g., a biolopolymeric array, such as a nucleic acid or polypeptide array.

BRIEF DESCRIPTION OF THE DRAWINGS

FIG. 3 schematically illustrates an embodiment of an array reader of the present invention.

FIG. 9 illustrates a substrate carrying multiple arrays.

FIG. 10 is an enlarged view of a portion of FIG. 9 showing multiple spots or features.

FIG. 11 is an enlarged illustration of a portion of the substrate in FIG. 10.

DEFINITIONS

Figure 1:
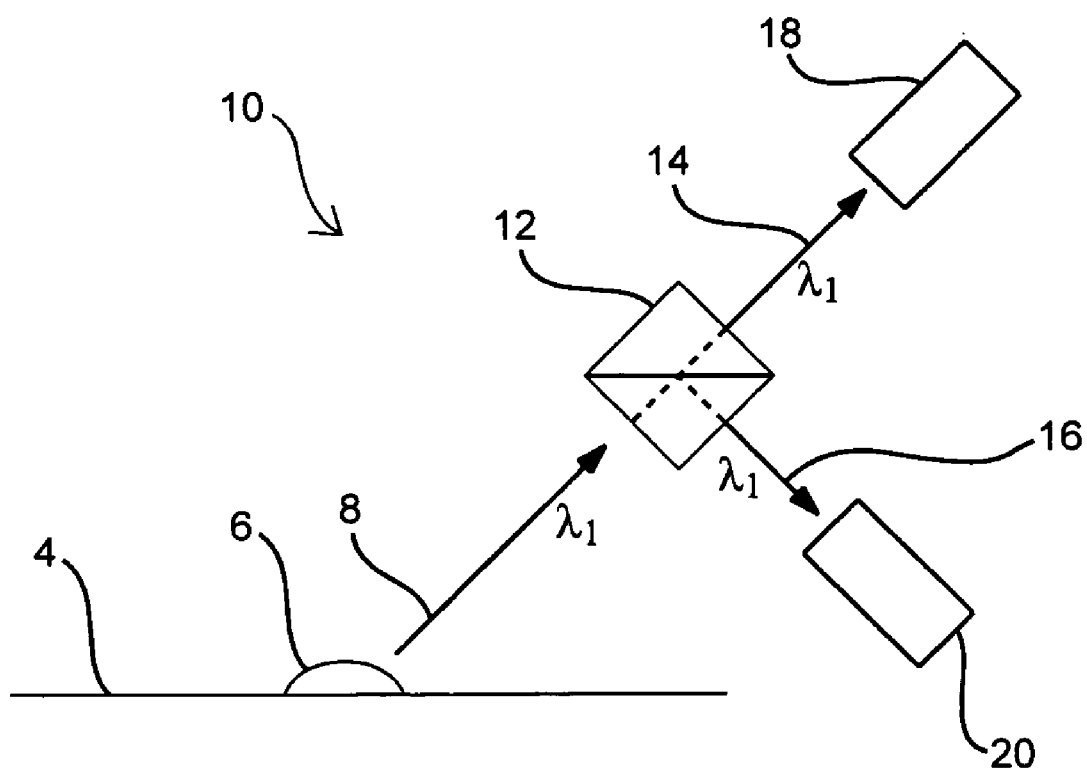
FIG. 1 schematically illustrates general features of an embodiment of a wide dynamic range detector system of the subject invention.

Unless defined otherwise, all technical and scientific terms used herein have the same meaning as commonly understood by one of ordinary skill in the art to which this invention belongs. Still, certain elements are defined below for the sake of clarity and ease of reference.

The term "polymer" means any compound that is made up of two or more monomeric units covalently bonded to each other, where the monomeric units may be the same or different, such that the polymer may be a homopolymer or a heteropolymer. Representative polymers include peptides, polysaccharides, nucleic acids and the like, where the polymers may be naturally occurring or synthetic. The term "biomolecule" means any organic or biochemical molecule, group or species of interest that may be formed in an array on a substrate surface. Exemplary biomolecules include peptides, proteins, amino acids and nucleic acids.

A "biopolymer" is a polymer of one or more types of repeating units. Biopolymers are typically found in biological systems (although they may be made synthetically) and may include peptides or polynucleotides, as well as such compounds composed of or containing amino acid analogs or non-amino acid groups, or nucleotide analogs or non-nucleotide groups. This includes polynucleotides in which the conventional backbone has been replaced with a non-naturally occurring or synthetic backbone, and nucleic acids (or synthetic or naturally occurring analogs) in which one or more of the conventional bases has been replaced with a group (natural or synthetic) capable of participating in Watson-Crick type hydrogen bonding interactions. For example, a "biopolymer" may include DNA (including cDNA), RNA, oligonucleotides, and PNA and other polynucleotides as described in U.S. Pat. No. 5,948,902 and references cited therein (all of which are incorporated herein by reference), regardless of the source. A "biomonomer" references a single unit, which can be linked with the same or other biomonomers to form a biopolymer (e.g., a single amino acid or nucleotide with two linking groups, one or both of which may have removable protecting groups).

The term "peptide" as used herein refers to any polymer compound produced by amide formation between an α-carboxyl group of one amino acid and an α-amino group of another group.

The term "oligopeptide" as used herein refers to peptides with fewer than about 10 to 20 residues, i.e. amino acid monomeric units.

The term "polypeptide" as used herein refers to peptides with more than 10 to 20 residues.

The term "protein" as used herein refers to polypeptides of specific sequence of more than about 50 residues and includes D and L forms, modified forms, etc. The terms "polypeptide" and "protein" may be used interchangeably.

The term "nucleic acid" as used herein means a polymer composed of nucleotides, e.g., deoxyribonucleotides or ribonucleotides, or compounds produced synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions.

The term "polynucleotide" as used herein refers to single- or double-stranded polymers composed of nucleotide monomers of generally greater than about 100 nucleotides in length. Polynucleotides include single or multiple stranded configurations, where one or more of the strands may or may not be completely aligned with another The terms "ribonucleic acid" and "RNA" as used herein mean a polymer composed of ribonucleotides.

The terms "deoxyribonucleic acid" and "DNA" as used herein mean a polymer composed of deoxyribonucleotides.

The term "oligonucleotide" as used herein denotes single-stranded nucleotide multimers of from about 10 to about 200 nucleotides in length, such as from about 25 to about 175 nucleotides in length, including from about 50 to about 160 nucleotides in length, e.g., 150 nucleotides in length.

The term "oligomer" is used herein to indicate a chemical entity that contains a plurality of monomers. As used herein, the terms "oligomer" and "polymer" are used interchangeably, as it is generally, although not necessarily, smaller "polymers" that are prepared using the functionalized substrates of the invention, particularly in conjunction with combinatorial chemistry techniques. Examples of oligomers and polymers include polydeoxyribonucleotides (DNA), polyribonucleotides (RNA), other polynucleotides which are C-glycosides of a purine or pyrimidine base, polypeptides (proteins), polysaccharides (starches, or polysugars), and other chemical entities that contain repeating units of like chemical structure. In the practice of the instant invention, oligomers will generally comprise about 2-50 monomers, preferably about 2-20, more preferably about 3-10 monomers.

The term "monomer" as used herein refers to a chemical entity that can be covalently linked to one or more other such entities to form a polymer. Of particular interest to the present application are nucleotide "monomers" that have first and second sites (e.g., 5' and 3' sites) suitable for binding to other like monomers by means of standard chemical reactions (e.g., nucleophilic substitution), and a diverse element which distinguishes a particular monomer from a different monomer of the same type (e.g., a nucleotide base, etc.). In the art synthesis of nucleic acids of this type utilizes an initial substrate-bound monomer that is generally used as a building-block in a multi-step synthesis procedure to form a complete nucleic acid.

The term "ligand" as used herein refers to a moiety that is capable of covalently or otherwise chemically binding a compound of interest. The arrays of solid-supported ligands produced by the methods can be used in screening or separation processes, or the like, to bind a component of interest in a sample. The term "ligand" in the context of the invention may or may not be an "oligomer" as defined above. However, the term "ligand" as used herein may also refer to a compound that is "pre-synthesized" or obtained commercially, and then attached to the substrate.

The term "sample" as used herein relates to a material or mixture of materials, typically, although not necessarily, in fluid form, containing one or more components of interest.

The terms "nucleoside" and "nucleotide" are intended to include those moieties which contain not only the known purine and pyrimidine bases, but also other heterocyclic bases that have been modified. Such modifications include methylated purines or pyrimidines, acylated purines or pyrimidines, alkylated riboses or other heterocycles. In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like.

As used herein, the term "amino acid" is intended to include not only the L, D- and nonchiral forms of naturally occurring amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine), but also modified amino acids, amino acid analogs, and other chemical compounds which can be incorporated in conventional oligopeptide synthesis, e.g., 4-nitrophenylalanine, isoglutamic acid, isoglutamine, $\epsilon$-nicotinoyl-lysine, isonipecotic acid, tetrahydroisoquinoleic acid, $\alpha$-aminoisobutyric acid, sarcosine, citrulline, cysteic acid, t-butylglycine, t-butylalanine, phenylglycine, cyclohexylalanine, $\beta$-alanine, 4-aminobutyric acid, and the like.

"Optional" or "optionally" means that the subsequently described circumstance may or may not occur, so that the description includes instances where the circumstance occurs and instances where it does not.

An "array," or "chemical array' used interchangeably includes any one-dimensional, two-dimensional or substantially two-dimensional (as well as a three-dimensional) arrangement of addressable regions bearing a particular chemical moiety or moieties (such as ligands, e.g., biopolymers such as polynucleotide or oligonucleotide sequences (nucleic acids), polypeptides (e.g., proteins), carbohydrates, lipids, etc.) associated with that region. In the broadest sense, the arrays of many embodiments are arrays of polymeric binding agents, where the polymeric binding agents may be any of: polypeptides, proteins, nucleic acids, polysaccharides, synthetic mimetics of such biopolymeric binding agents, etc. In many embodiments of interest, the arrays are arrays of nucleic acids, including oligonucleotides, polynucleotides, cDNAs, mRNAs, synthetic mimetics thereof, and the like. Where the arrays are arrays of nucleic acids, the nucleic acids may be covalently attached to the arrays at any point along the nucleic acid chain, but are generally attached at one of their termini (e.g. the 3' or 5' terminus). Sometimes, the arrays are arrays of polypeptides, e.g., proteins or fragments thereof.

Any given substrate may carry one, two, four or more or more arrays disposed on a front surface of the substrate. Depending upon the use, any or all of the arrays may be the same or different from one another and each may contain multiple spots or features. A typical array may contain more than ten, more than one hundred, more than one thousand more ten thousand features, more than one hundred thousand features, or even more than one million features, in an area of less than 20 $cm^2$ or even less than 10 $cm^2$. For example, features may have widths (that is, diameter, for a round spot) in the range from a 10 $\mu$m to 1.0 cm. In other embodiments each feature may have a width in the range of 1.0 $\mu$m to 1.0 mm, usually 5.0 $\mu$m to 500 $\mu$m, and more usually 10 $\mu$m to 200 $\mu$m. Non-round features may have area ranges equivalent to that of circular features with the foregoing width (diameter) ranges. At least some, or all, of the features are of different compositions (for example, when any repeats of each feature composition are excluded the remaining features may account for at least 5%, 10%, or 20% of the total number of features). Interfeature areas will typically (but not essentially) be present which do not carry any polynucleotide (or other biopolymer or chemical moiety of a type of which the features are composed). Such interfeature areas typically will be present where the arrays are formed by processes involving drop deposition of reagents but may not be present when, for example, light directed synthesis fabrication processes are used. It will be appreciated though, that the interfeature areas, when present, could be of various sizes and configurations.

Each array may cover an area of less than 100 $cm^2$, or even less than 50 $cm^2$, 10 $cm^2$ or 1 $cm^2$. In many embodiments, the substrate carrying the one or more arrays will be shaped generally as a rectangular solid (although other shapes are possible), having a length of more than 4 mm and less than 1 m, such as more than 4 mm and less than 600 mm, and including less than 100 mm; a width of more than 4 mm and less than 1 m, such as less than 500 mm, and including less than 50 mm; and a thickness of more than 0.01 mm and less than 5.0 mm, such as more than 0.1 mm and less than 2 mm and more including more than 0.2 and less than 1.5 mm. With arrays that are read by detecting fluorescence, the substrate may be of a material that emits low fluorescence upon illumination with the excitation light. Additionally in this situation, the substrate may be relatively transparent to reduce the absorption of the incident illuminating laser light and subsequent heating if the focused laser beam travels too slowly over a region. For example, substrate 10 may transmit at least 20%, or 50% (or even at least 70%, 90%, or 95%), of the illuminating light incident on the front as may be measured across the entire integrated spectrum of such illuminating light or alternatively at 532 nm or 633 nm. The substrate can be porous or non-porous. The substrate can be planar or non-planar.

Arrays may be fabricated using drop deposition from pulse jets of either precursor units (such as nucleotide or amino acid monomers) in the case of in situ fabrication, or the previously obtained biomolecule, e.g., polynucleotide. Such methods are described in detail in, for example, the previously cited references including U.S. Pat. Nos. 6,242,266, 6,232,072, 6,180,351, 6,171,797, 6,323,043, U.S. patent application Ser. No. 09/302,898 filed Apr. 30, 1999 by Caren et al., and the references cited therein. Other drop deposition methods can be used for fabrication, as previously described herein.

An exemplary chemical array is shown in FIGS. 9-11, where the array shown in this representative embodiment includes a contiguous planar substrate 110 carrying an array 112 disposed on a rear surface 111b of substrate 110. It will be appreciated though, that more than one array (any of which are the same or different) may be present on rear surface 111b, with or without spacing between such arrays. That is, any given substrate may carry one, two, four or more arrays disposed on a front surface of the substrate and depending on the use of the array, any or all of the arrays may be the same or different from one another and each may contain multiple spots or features. The one or more arrays 112 may cover only a portion of the rear surface 111b, with regions of the rear surface 111b adjacent the opposed sides 113c, 113d and leading end 113a and trailing end 113b of slide 110, not being covered by any array 112. A front surface 111a of the slide 110 does not carry any arrays 112. Each array 112 can be designed for testing against any type of sample, whether a trial sample, reference sample, a combination of them, or a known mixture of biopolymers such as polynucleotides. Substrate 110 may be of any shape, as mentioned above.

As mentioned above, array 112 contains multiple spots or features 116 of biopolymers, e.g., in the form of polynucleotides. As mentioned above, all of the features 116 may be different, or some or all could be the same. The interfeature areas 117 could be of various sizes and configurations. Each feature carries a predetermined biopolymer such as a predetermined polynucleotide (which includes the possibility of mixtures of polynucleotides). It will be understood that there may be a linker molecule (not shown) of any known types between the rear surface 111b and the first nucleotide.

Substrate 110 may carry on front surface 111a, an identification code, e.g., in the form of bar code (not shown) or the like printed on a substrate in the form of a paper label attached by adhesive or any convenient means. The identification code contains information relating to array 112, where such information may include, but is not limited to, an identification of array 112, i.e., layout information relating to the array(s), etc.

In those embodiments where an array includes two more features immobilized on the same surface of a solid support, the array may be referred to as addressable. An array is "addressable" when it has multiple regions of different moieties (e.g., different polynucleotide sequences) such that a region (i.e., a "feature" or "spot" of the array) at a particular predetermined location (i.e., an "address") on the array will detect a particular target or class of targets (although a feature may incidentally detect non-targets of that feature). Array features are typically, but need not be, separated by intervening spaces. In the case of an array, the "target" will be referenced as a moiety in a mobile phase (typically fluid), to be detected by probes ("target probes") which are bound to the substrate at the various regions. However, either of the "target" or "probe" may be the one which is to be evaluated by the other (thus, either one could be an unknown mixture of analytes, e.g., polynucleotides, to be evaluated by binding with the other).

An array "assembly" includes a substrate and at least one chemical array, e.g., on a surface thereof. Array assemblies may include one or more chemical arrays present on a surface of a device that includes a pedestal supporting a plurality of prongs, e.g., one or more chemical arrays present on a surface of one or more prongs of such a device. An assembly may include other features (such as a housing with a chamber from which the substrate sections can be removed). "Array unit" may be used interchangeably with "array assembly".

"Hybridizing" and "binding", with respect to polynucleotides, are used interchangeably.

The term "substrate" as used herein refers to a surface upon which marker molecules or probes, e.g., an array, may be adhered. Glass slides are the most common substrate for biochips, although fused silica, silicon, plastic and other materials are also suitable. As mentioned above, the substrate may be planar or non-planar. The substrate may be porous or non-porous.

When two items are "associated" with one another they are provided in such a way that it is apparent one is related to the other such as where one references the other. For example, an array identifier can be associated with an array by being on the array assembly (such as on the substrate or a housing) that carries the array or on or in a package or kit carrying the array assembly. "Stably attached" or "stably associated with" means an item's position remains substantially constant where in certain embodiments it may mean that an item's position remains substantially constant and known.

A "web" references a long continuous piece of substrate material having a length greater than a width. For example, the web length to width ratio may be at least 5:1, 10:1, 50:1, 100:1, 200:1, or 500:1, or even at least 1000:1.

"Flexible" with reference to a substrate or substrate web, references that the substrate can be bent 180 degrees around a roller of less than 1.25 cm in radius. The substrate can be so bent and straightened repeatedly in either direction at least 100 times without failure (for example, cracking) or plastic deformation. This bending must be within the elastic limits of the material. The foregoing test for flexibility is performed at a temperature of 20° C.

"Rigid" refers to a material or structure which is not flexible, and is constructed such that a segment about 2.5 by 7.5 cm retains its shape and cannot be bent along any direction more than 60 degrees (and often not more than 40, 20, 10, or 5 degrees) without breaking.

A "scan region" refers to a contiguous (preferably, rectangular) area in which the array spots or features of interest, as defined above, are found. The scan region is that portion of the total area illuminated from which the resulting fluorescence is detected and recorded. For the purposes of this invention, the scan region includes the entire area of the slide scanned in each pass of the lens, between the first feature of interest, and the last feature of interest, even if there exist intervening areas which lack features of interest. An "array layout" refers to one or more characteristics of the features, such as feature positioning on the substrate, one or more feature dimensions, and an indication of a moiety at a given location. "Hybridizing" and "binding", with respect to polynucleotides, are used interchangeably.

The terms "hybridizing specifically to" and "specific hybridization" and "selectively hybridize to," as used herein refer to the binding, duplexing, or hybridizing of a nucleic acid molecule preferentially to a particular nucleotide sequence under stringent conditions.

The term "stringent assay conditions" as used herein refers to conditions that are compatible to produce binding pairs of nucleic acids, e.g., surface bound and solution phase nucleic acids, of sufficient complementarity to provide for the desired level of specificity in the assay while being less compatible to the formation of binding pairs between binding members of insufficient complementarity to provide for the desired specificity. Stringent assay conditions are the summation or combination (totality) of both hybridization and wash conditions.

"Stringent hybridization conditions" and "stringent hybridization wash conditions" in the context of nucleic acid hybridization (e.g., as in array, Southern or Northern hybridizations) are sequence dependent, and are different under different experimental parameters. Stringent hybridization conditions that can be used to identify nucleic acids within the scope of the invention can include, e.g., hybridization in a buffer comprising 50% formamide, 5×SSC, and 1% SDS at 42° C., or hybridization in a buffer comprising 5×SSC and 1% SDS at 65° C., both with a wash of 0.2×SSC and 0.1% SDS at 65° C. Exemplary stringent hybridization conditions can also include a hybridization in a buffer of 40% formamide, 1 M NaCl, and 1% SDS at 37° C., and a wash in 1×SSC at 45° C. Alternatively, hybridization to filter-bound DNA in 0.5 M NaHPO$_4$, 7% sodium dodecyl sulfate (SDS), 1 mM EDTA at 65° C., and washing in 0.1×SSC/0.1% SDS at 68° C. can be employed. Yet additional stringent hybridization conditions include hybridization at 60° C. or higher and 3×SSC (450 mM sodium chloride/45 mM sodium citrate) or incubation at 42° C. in a solution containing 30% formamide, 1 M NaCl, 0.5% sodium sarcosine, 50 mM MES, pH 6.5. Those of ordinary skill will readily recognize that alternative but comparable hybridization and wash conditions can be utilized to provide conditions of similar stringency.

In certain embodiments, the stringency of the wash conditions sets forth the conditions which determine whether a nucleic acid is specifically hybridized to a surface bound nucleic acid. Wash conditions used to identify nucleic acids may include, e.g.: a salt concentration of about 0.02 molar at pH 7 and a temperature of at least about 50° C. or about 55° C. to about 60° C.; or, a salt concentration of about 0.15 M NaCl at 72° C. for about 15 minutes; or, a salt concentration of about 0.2×SSC at a temperature of at least about 50° C. or about 55° C. to about 60° C. for about 15 to about 20 minutes; or, the hybridization complex is washed twice with a solution with a salt concentration of about 2×SSC containing 0.1% SDS at room temperature for 15 minutes and then washed twice by 0.1×SSC containing 0.1% SDS at 68° C. for 15 minutes; or, equivalent conditions. Stringent conditions for washing can also be, e.g., 0.2×SSC/0.1% SDS at 42° C.

A specific example of stringent assay conditions is rotating hybridization at 65° C. in a salt based hybridization buffer with a total monovalent cation concentration of 1.5 M (e.g., as described in U.S. patent application Ser. No. 09/655,482 filed on Sep. 5, 2000, the disclosure of which is herein incorporated by reference) followed by washes of 0.5×SSC and 0.1× SSC at room temperature.

Stringent assay conditions are hybridization conditions that are at least as stringent as the above representative conditions, where a given set of conditions are considered to be at least as stringent if substantially no additional binding complexes that lack sufficient complementarity to provide for the desired specificity are produced in the given set of conditions as compared to the above specific conditions, where by "substantially no more" is meant less than about 5-fold more, typically less than about 3-fold more. Other stringent hybridization conditions are known in the art and may also be employed, as appropriate.

"Contacting" means to bring or put together. As such, a first item is contacted with a second item when the two items are brought or put together, e.g., by touching them to each other.

"Depositing" means to position, place an item at a location- or otherwise cause an item to be so positioned or placed at a location. Depositing includes contacting one item with another. Depositing may be manual or automatic, e.g., "depositing" an item at a location may be accomplished by automated robotic devices.

By "remote location," it is meant a location other than the location at which the array (or referenced item) is present and hybridization occurs (in the case of hybridization reactions). For example, a remote location could be another location (e.g., office, lab, etc.) in the same city, another location in a different city, another location in a different state, another location in a different country, etc. As such, when one item is indicated as being "remote" from another, what is meant is that the two items are at least in different rooms or different buildings, and may be at least one mile, ten miles, or at least one hundred miles apart.

"Communicating" information means transmitting the data representing that information as signals (e.g., electrical, optical, radio signals, and the like) over a suitable communication channel (for example, a private or public network).

"Forwarding" an item refers to any means of getting that item from one location to the next, whether by physically transporting that item or otherwise (where that is possible) and includes, at least in the case of data, physically transporting a medium carrying the data or communicating the data.

An array "package" may be the array plus only a substrate on which the array is deposited, although the package may include other features (such as a housing with a chamber). A "chamber" references an enclosed volume (although a chamber may be accessible through one or more ports). It will also be appreciated that throughout the present application, that words such as "top," "upper," and "lower" are used in a relative sense only.

It will also be appreciated that throughout the present application, that words such as "cover", "base" "front", "back", "top", are used in a relative sense only. The word "above" used to describe the substrate and/or flow cell is meant with respect to the horizontal plane of the environment, e.g., the room, in which the substrate and/or flow cell is present, e.g., the ground or floor of such a room.

A "computer-based system" refers to the hardware means, software means, and data storage means used to analyze the information of the present invention. The minimum hardware of the computer-based systems of the present invention comprises a central processing unit (CPU), input means, output means, and data storage means. A skilled artisan can readily appreciate that many computer-based systems are available which are suitable for use in the present invention. The data storage means may comprise any manufacture comprising a recording of the present information as described above, or a memory access means that can access such a manufacture.

A "processor" references any hardware and/or software combination which will perform the functions required of it. For example, any processor herein may be a programmable digital microprocessor such as available in the form of an electronic controller, mainframe, server or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic medium or optical disk may carry the programming, and can be read by a suitable reader communicating with each processor at its corresponding station.

"Computer readable medium" as used herein refers to any storage or transmission medium that participates in providing instructions and/or data to a computer for execution and/or processing. Examples of storage media include floppy disks, magnetic tape, UBS, CD-ROM, a hard disk drive, a ROM or integrated circuit, a magneto-optical disk, or a computer readable card such as a PCMCIA card and the like, whether or not such devices are internal or external to the computer. A file containing information may be "stored" on computer readable medium, where "storing" means recording information such that it is accessible and retrievable at a later date by a computer. A file may be stored in permanent memory.

With respect to computer readable media, "permanent memory" refers to memory that is permanently stored on a data storage medium. Permanent memory is not erased by termination of the electrical supply to a computer or processor. Computer hard-drive ROM (i.e. ROM not used as virtual memory), CD-ROM, floppy disk and DVD are all examples of permanent memory. Random Access Memory (RAM) is an example of non-permanent memory. A file in permanent memory may be editable and re-writable.

To "record" data, programming or other information on a computer readable medium refers to a process for storing information, using any such methods as known in the art. Any convenient data storage structure may be chosen, based on the means used to access the stored information. A variety of data processor programs and formats can be used for storage, e.g. word processing text file, database format, etc.

A "memory" or "memory unit" refers to any device which can store information for subsequent retrieval by a processor, and may include magnetic or optical devices (such as a hard disk, floppy disk, CD, or DVD), or solid state memory devices (such as volatile or non-volatile RAM). A memory or memory unit may have more than one physical memory device of the same or different types (for example, a memory may have multiple memory devices such as multiple hard drives or multiple solid state memory devices or some combination of hard drives and solid state memory devices).

Items of data are "linked" to one another in a memory when the same data input (for example, filename or directory name or search term) retrieves the linked items (in a same file or not) or an input of one or more of the linked items retrieves one or more of the others.

A "reader" or "scanner" is a device for evaluating arrays. In representative readers, an optical light source, such as a laser light source, generates a collimated beam. The collimated beam is focused on the array and sequentially illuminates small surface regions of known location (i.e., a position) on an array substrate. The resulting signals from the surface regions are typically collected using a confocal system (gathering the array image on a point-by-point basis) or via an imaging system (collecting signals from an extended area on the array). In either case, the collected signals are filtered using an appropriate dichroic filter, or set of filters, to discriminate between fluorescence from the dye molecules and light at the excitation wavelength. A recording device, such as a computer memory, records the detected signals and builds up a raster scan file of intensities as a function of position, or time as it relates to the position. Such intensities, as a function of position, are typically referred to in the art as "pixels". Arrays are often scanned and/or scan results are often represented at 2-50 micron pixel resolution, and such as at 2-20 micron resolution, and including at 2-10 micron spatial resolution. To achieve the precision required for such activity, components such as the lasers must be set and maintained with particular alignment. Scanners may be bi-directional, or unidirectional, as is known in the art. A reader typically used for the evaluation of arrays includes a scanning fluorometer. A number of different types of such devices are commercially available from different sources, such as Perkin-Elmer, Agilent, or Axon Instruments, etc., and examples of typical scanners are described in U.S. Pat. Nos. 5,091,652; 5,760,951, 6,320,196 and 6,355,934.

The terms "assessing" and "evaluating" are used interchangeably to refer to any form of measurement, and include determining if an element is present or not. The terms "determining," "measuring," and "assessing," and "assaying" are used interchangeably and include both quantitative and qualitative determinations. Assessing may be relative or absolute. "Assessing the presence of" includes determining the amount of something present, as well as determining whether it is present or absent. The term "evaluating a pixel" and grammatical equivalents thereof, are used to refer to measuring the strength, e.g., magnitude, of pixel signal to determine the brightness of a corresponding area present on the surface of an object scanned.

A "processor" references any hardware and/or software combination which will perform the functions required of it. For example, any processor herein may be a programmable digital microprocessor such as available in the form of an electronic controller, mainframe, server or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic medium or optical disk may carry the programming, and can be read by a suitable reader communicating with each processor at its corresponding station. In certain embodiments, a processor may be a "signal processor", where a signal processor receives input signals and processes those signals. A signal processor may be programmed or hard wired to perform one or more mathematical functions, such as those described below. In certain embodiments, a signal processor may "integrate" a set of digital signals (e.g., a set of digital signals representing an analog signal or a digitized version of an analog signal) to produce an integrated data signal.

By "integrating" is meant that a set of digital signals is input into a signal processor and the signal processor provides an output signal, where in certain embodiments a single output signal represents the set of input signals. In representative embodiments, the input set of digital signals may be integrated by summing the set of input signals, however, other means for integrating (e.g., averaging, etc.) are well known in the art. If an analog signal is referred to as being integrated, then it is understood that the analog signal is first digitized (i.e., sampled) prior to integration. For example, if an analog signal for a pixel is to be integrated, the signal is first sampled and digitized to provide a set of digital signals, and those digital signals are integrated by a signal processor to provide an output signal, typically a binary signal that represents a numerical evaluation of the overall magnitude of the input set of digital signals (thereby providing a numerical evaluation of the magnitude of the analog signal for the pixel). The output of a signal processor may be referred herein as "data" and may be stored in memory.

Data from reading an array may be raw data (such as fluorescence intensity readings for each feature in one or more color channels, or for example, the output of a signal processor that has integrated a set of digital signals for a pixel) or may be processed data such as obtained by rejecting a reading for a feature which is below a predetermined threshold and/or forming conclusions based on the pattern read from the array (such as whether or not a particular target sequence may have been present in the sample). The data obtained from an array reading (processed or not) may be forwarded (such as by communication) to a remote location if desired, and received there for further use (such as further processing). Stated otherwise, in certain variations, the subject methods may include a step of transmitting data from at least one of the detecting and deriving steps, to a remote location. The data may be transmitted to the remote location for further evaluation and/or use. Any convenient telecommunications means may be employed for transmitting the data, e.g., facsimile, modem, internet, etc. Data may represent a floating point number or integer, for example.

A set of digital signals for a pixel (or an analog signal represented thereby) may be "saturated", "partially-saturated" or "non-saturated" depending on the number of saturated digital signals within the set. The digital signals in a saturated set of digital signals are all saturated, none of the digital signals in a non-saturated set of digital signals are saturated, and some but not all of the digital signals within a partially-saturated set of digital signals are saturated. Saturated digital signals may be identified by virtue of the fact that they are at maximal magnitude, and non-saturated digital signals may be identified by virtue of the fact that they are below maximal magnitude.

The term sensitivity when used in describing a detector refers to the detector's ability to detect light of a given intensity, with high sensitivity detectors being able to detect low intensity light, where such detectors may be saturated at higher light intensities) and low sensitivity detectors being to detect higher intensity light without saturation. By light intensity is meant the amount of energy, e.g., in the form of photons, per unit area in a signal, e.g., detected at a detector.

A "predetermined wavelength of light" is detectable light of a particular wavelength emitted by a label that indicates the presence of the label. A particular wavelength of light may contain a range of wavelengths (e.g. +/−5 nm or more) that contains the wavelength at which emission of the label is at a maximum.

The term "using" has its conventional meaning, and, as such, means employing, e.g., putting into service, a method or composition to attain an end. For example, if a program is used to create a file, a program is executed to make a file, the file usually being the output of the program. In another example, if a computer file is used, it is usually accessed, read, and the information stored in the file employed to attain an end. Similarly if a unique identifier, e.g., a barcode is used, the unique identifier is usually read to identify, for example, an object or file associated with the unique identifier.

A system that contains a "first detector" and a "second detector" may contain additional detectors (e.g., a third or a fourth detector)

The term "providing" encompasses such terms as "generating", "identifying" and "producing".

DETAILED DESCRIPTION

A system for detecting a predetermined wavelength of light emitted from an area on the surface of a biopolymeric array is provided. Aspects of the system include: (a) a beam splitter that is configured for splitting the light emitted from the surface, e.g., laser induced fluorescence (LIF), into a first and second light beam (b) a first detector for detecting photons in the first light beam, and (c) a second detector for detecting photons in the second light beam. In certain embodiments, the system may include a processing system for integrating and outputting numerical information representing the light signal detected by the first and second detectors. Also provided are methods of detecting light using the subject system, programming for performing the subject methods and an array reader containing the subject system. A kit for retrofitting an array reader is also provided. The subject invention finds use in a variety of different applications, including genomics, proteomics, and bioinformatics applications.

Before the present invention is described in such detail, however, it is to be understood that this invention is not limited to particular variations set forth and may, of course, vary. Various changes may be made to the invention described and equivalents may be substituted without departing from the true spirit and scope of the invention. In addition, many modifications may be made to adapt a particular situation, material, composition of matter, process, process act(s) or step(s), to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As summarized above, the invention provides a wide dynamic range detector system (for instance, a multi-detector system) for detecting light (e.g., of a pre-determined wavelength) emitted from an area on a surface of a chemical array. By "dynamic range" is meant the range of light signal intensity that can be detected by a detector, without signal saturation or production of a signal that is not significantly above background. By signal intensity is meant the amount of energy, e.g., in the form of photons, per unit area in a signal, e.g., detected at a detector. By "wide dynamic range" is meant that the range of light signal intensity that can be detected (i.e., by a reader of the subject invention) is increased beyond that which can be detected by an array reader employing a single detector alone. This means that, in comparison to a reader that employs a single detector for a particular wavelength of light, a reader of the subject invention is both more sensitive to light signals of lower intensity, allowing it to better distinguish positive signals from background noise, and additionally less sensitive to light signals of higher intensity, allowing it to detect light signals of higher intensity without becoming saturated. Hence, by using the teachings of the subject invention, the dynamic range of a reader may be increased by at least 10-fold, 100-fold, $1\times10^3$-fold, $1\times10^4$-fold, $1\times10^5$-fold, $1\times10^6$-fold, $1\times10^7$-fold, $1\times10^8$-fold or more relative to a reader containing a single detector.

For purposes of clarity and illustration, without any intention to be limited hereby, a wide dynamic range detector system will be described with respect to a multi-detector system that, when configured in accordance with the teachings herein disclosed, increases the overall dynamic range of a detector system, for instance, a detector system using only one detector for a particular wavelength of light. While the number of detectors that could be employed may vary, the general features of the invention will be described with reference to a system containing two detectors for ease of illustration. By "multi-detector system" is meant a system that contains at least two detectors, e.g., three, four, five, six, ten, or twenty or more detectors, depending on how the system is configured. It is also to be understood that one skilled in the art could readily configure the exemplified system to add further detectors and other optical components such as beam splitters without undue effort. Accordingly, the following description should not limit the invention to one that contains or employs two detectors.

In general terms, the system includes: a) a beam splitter and b) at least two detectors (i.e., a first detector and a second detector) that have different dynamic ranges of detection (e.g., for instance, overlapping dynamic ranges). The beam splitter splits light of a pre-determined wavelength emitted from a surface of a chemical array into two beams. The detectors then evaluate the intensity of that light of the pre-determined wavelength to produce data. Generally, for a single wavelength of light (e.g., a single "channel", e.g., a "green" or "red" channel), at least two sets of data are obtained from a reading of an array: a first set of data obtained from the first detector and a second set of data obtained from the second detector. The "best" data points, i.e., data points that are neither at the upper limit (i.e., saturated) nor at the lower limit of detection (i.e., not significantly above background), are selected from the first and second sets of data and combined to provide a final data set.

For example (and as will be described in greater detail below), in certain cases a data point for a "bright" pixel may be saturated in the data set produced using the more sensitive detector and not saturated in the data set produced using the less sensitive detector. If this is the case, the data point produced using the less sensitive detector may be selected for inclusion in the final data set. Likewise, a data point for a "dim" pixel (i.e., a pixel that has a low signal) may not be above background in the data set produced using the less sensitive detector and significantly above background in the data set produced using the more sensitive detector. In this case, the data point produced using the most sensitive detector may be selected for inclusion in the final data set. In other words, the subject system may be employed to effectively increase the dynamic range of an array reader by reading an array using two detectors, and combining the data produced using the detectors. When combined, the data sets may be "normalized" as desired in producing the final data set.

By using a subject multi-detector system, the dynamic range of a reader may be increased by at least 10-fold, 100-fold, $1\times10^3$-fold, $1\times10^4$-fold, $1\times10^5$-fold, $1\times10^6$-fold, $1\times10^7$-fold, $1\times10^8$-fold or more, relative to a reader containing a single detector. A reader of the invention, as described below, may have a dynamic range from of at least about 1 to about $1\times10^5$ at least about 1 to at least about $1\times10^6$, at least about 1 to at least about $1\times10^7$, at least about 1 to at least about $1\times10^8$ or more, depending on the exact components used.

The detectors employed in the system generally have different sensitivities in that they have different dynamic ranges, where the "dynamic range" of a detector refers to the range of light signal intensity that can be detected by a detector, without signal saturation or production of a signal that is not significantly above background. In one embodiment, the two detectors have an overlapping dynamic range, however, the dynamic ranges of the two detectors need not overlap. The dynamic range of a detector is measured from the maximum amplitude of light signal strength that can be detected without becoming saturated to the minimum detectable value the detector can detect above the background.

In certain embodiments, the detectors used in the system either a) have an inherent difference in their ability to detect emitted light at the pre-determined wavelength (e.g., because different types of detectors are used) or b) are set using different gains, where "gain" refers to the amount by which an input signal is amplified by the detector. By modulating the gain of a detector an operator can modulate the sensitivity of that detector to emitted light.

In one embodiment, the more sensitive detector of the subject system may have a dynamic range that allows it to distinguish weak light signals from background signals. However, such a detector may produce a saturated signal for high intensity light. The less sensitive detector of the subject system may have a dynamic range that allows it to produce a non-saturated signal when detecting high intensity light. However, because of its lower sensitivity, such a detector may not be able to distinguish a low intensity signal from background noise. By employing two detectors of differing sensitivities in one array reader, the overall dynamic range the reader may be increased and a more accurate reading of an array, as compared to a reader containing a single detector.

The general features of one aspect of the invention may be described with reference to FIG. 1. In one embodiment, the invention provides a system 10 and a method for using the system for detecting light emitted from an area on the surface of a chemical array. By "area" of an array is meant a region that is the subject of detection by the subject multi-detector system. An area of an array may be as small as a single pixel or as broad as one or more features, dependent upon how the system is configured. In one embodiment, an area corresponds to the dimensions of a pixel. The subject system includes a beam-splitter 12 and at least two detectors (18 and 20). Light 8 at a predetermined wavelength ($\lambda_1$), emitted from an area 6 of the array 4, is transmitted to the beam splitter 12 where it is split into first and second light beams 14 and 16, each containing light of the predetermined wavelength ($\lambda_1$) that are then detected by the first and second detectors 18 and 20, respectively. The outputs of detectors 18 and 20 are processed to produce data.

As noted above, a pre-determined wavelength of light is a wavelength of light that indicates the presence of a particular detectable label. In certain embodiments, therefore, the pre-determined wavelength of light corresponds to the wavelength of maximal energy emission from a light-emitting label, such as a fluorescent label. While the pre-determined wavelength of light may vary, in representative embodiments it ranges from about 400 to about 800 nm, such as from about 550 to about 610 nm and including from about 650 to about 750 nm. Pre-determined wavelengths of particular interest include, but are not limited to, the emission maxima of the following fluorescent labels: xanthene dyes, e.g., fluorescein and rhodamine dyes, such as fluorescein isothiocyanate (FITC), 6-carboxyfluorescein (commonly known by the abbreviations FAM and F), 6-carboxy-2',4',7',4,7-hexachlorofluorescein (HEX), 6-carboxy-4',5'-dichloro-2',7'-dimethoxyfluorescein (JOE or J), N,N,N',N'-tetramethyl-6-carboxyrhodamine (TAMRA or T), 6-carboxy-X-rhodamine (ROX or R), 5-carboxyrhodamine-6G ($R6G^5$ or $G^5$), 6-carboxyrhodamine-6G ($R6G^6$ or $G^6$), and rhodamine 110; cyanine dyes, e.g., Cy3, Cy5 and Cy7 dyes; coumarins, e.g umbelliferone; benzimide dyes, e.g. Hoechst 33258; phenanthridine dyes, e.g., Texas Red; ethidium dyes; acridine dyes; carbazole dyes; phenoxazine dyes; porphyrin dyes; polymethine dyes; BODIPY dyes and quinoline dyes.

The beam splitter employed in the subject methods is generally configured in such a way that a first portion, e.g., half, of the light at the pre-determined wavelength that strikes the face of the beam splitter is reflected toward one of the detectors (e.g., the first detector), and the remainder of the light at the pre-determined wavelength is transmitted toward the other detector (e.g., the second detector). In other words, the beam splitter employed neither reflects all of the light at the pre-determined wavelength, nor transmits all of the light at the pre-determined wavelength. Accordingly, in embodiments of particular interest, the beam splitter employed in the subject system may be an achromatic beam splitter in the wavelength region of interest. The beam splitter employed does not separate light at the pre-determined wavelength and light at other wavelengths, i.e., it is not a dichroic or chromatic beam splitter. Beam splitters that may be used in the subject invention are well known in the art and may be in a form that includes but is not limited to: a cube, a plate, a hexagon, pentagon, and may be polarizing or non-polarizing, narrowband, broadband, dielectric, air spaced, metal spaced, or the like. Representative beam splitters that may be employed are available for purchase from, but not limited hereto: LightMachinery [Ontario, Canada], Red Optronics [Mountain View, Calif.], or Stocker Yale [Salem, N.H.].

In certain embodiments, the first and second detectors may be the same type of detector or they may be different types of detectors. In general, the first detector may be configured for detecting low intensity light and a second detector may be configured to detect high intensity light. As such, the second detector may be configured to detect higher intensity light then the first detector, where the intensity of light detected by the second detector is at least about 10-fold, 100-fold, $1\times10^3$-fold, $1\times10^4$-fold, $1\times10^5$-fold, $1\times10^6$-fold, $1\times10^7$-fold, $1\times10^8$ fold greater than the intensity of light detected by the first detector. In certain embodiments, the gain of the detector(s) may be increased at least in proportion to the decrease in optical throughput that results from the insertion of the beam splitter. For example, if the beam splitter divides the optical beam in a ratio of 1:1 the initial gain should be doubled at a minimum.

If the first and second detectors 18 and 20 are the same type of detectors, the first detector 18 may be set at a higher gain than the second detector 20. For example, the first detector may have a gain set upwards to about a maximum (e.g., within 10% of the maximum gain), while the second detector may have a gain set lower to about a minimum (e.g., within 10% of the minimum gain). In one embodiment, the gain on the first and second detectors is set so that their individual dynamic ranges overlap, i.e., that is that the lower end of the dynamic range of the first detector over laps with the higher end of the dynamic range of the second detector. In this way, the overall dynamic range of the system may be increased.

If the first and second detectors 18 and 20 are of different types, one detector may be more sensitive and the other may be less sensitive, or they may be configured such that a first detector 18 detects low intensity light (because of its inherent sensitivities or because of its higher gain setting or both) and the second detector 20 detects high intensity light (because of its relative insensitivity or because of its lower gain setting or both). In one embodiment, the first and second detectors (e.g., 18 and 20) have an overlapping dynamic range and the more sensitive detector is set at a higher gain then the less sensitive detector. For instance, where the first detector is a PMT and the second detector is a SiPD, the overall dynamic range of the system may be as high as $10^8$.

The detectors employed herein may be any instrument capable of capturing an optical emission of energy (e.g., photons) and converting that energy into an analog and/or digital signal. For instance, one or more of the detectors may be a member of the group including a photo-multiplier tube (PMT), a photodiode (PD), a silicon photodiode (SiPD), an avalanche photodiode (APD), a charge-coupled device (CCD), a charge-injection device (CID), a complementary-metal-oxide-semiconductor detector (CMOS) device, a visible light photon counter, or the like.

In embodiments in which the detectors employed are of the same type, the detectors may each be PMT detectors, for example. In embodiments in which the detectors employed are of different types, one detector may be a PMT (having a dynamic range about $10^4$) and the other detector may be a SiPD detector (having with a dynamic range about $10^5$-$10^4$).

Figure 2A:
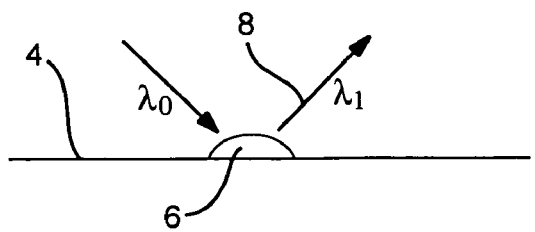
FIGS. 2A-2D provide a stepwise illustration of one embodiment of how a wide dynamic range detector system of the subject invention works.

FIGS. 2A-2D describe in greater detail than above how the subject system works. With reference to FIG. 2A, an array 4 containing a fluorescent area 6 upon its surface is placed within an array reader for scanning. A source of excitation energy, such as a laser, irradiates area 6 with light at excitatory wavelength $\lambda_0$. In response to the excitation energy the fluorescent area emits light 8 having a predetermined wavelength of $\lambda_1$.

Figure 2B:
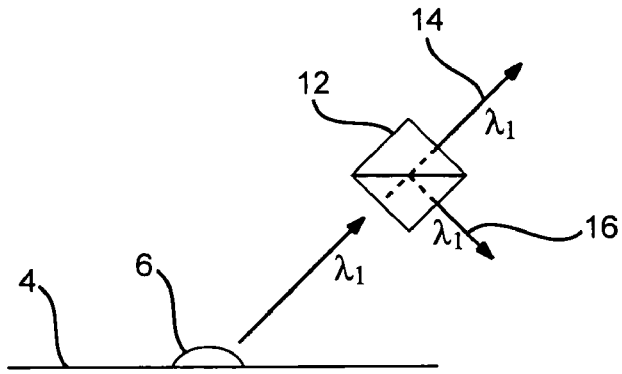

With reference to FIG. 2B, once an area of an array containing a sample has been irradiated to produce a light 8 of a predetermined wavelength $\lambda_1$, a portion of which is transmitted to a beam splitter 12 that is configured to split the light at the predetermined wavelength 8 (i.e., fluorescence at $\lambda_1$) into a first light beam 14 containing light at wavelength $\lambda_1$ and a second light beam 16 that also contains light at wavelength $\lambda_1$.

Figure 2C:
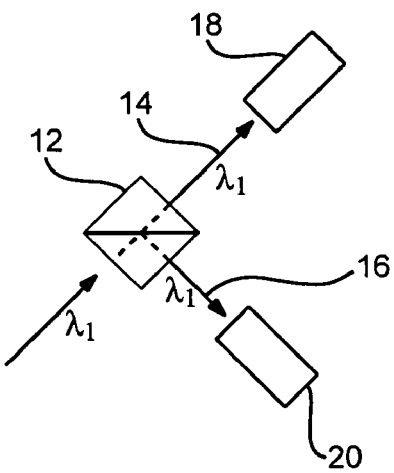

With reference to FIG. 2C, emitted light 8 enters the beam splitter 12 and is split into first and second light beams (14 and 16). Photons in the first light beam 14 are detected by the first detector 18, and photons in the second light beam 14 are detected by the second detector 20. As discussed above, the first and second detectors (e.g., 18 and 20) are each configured for receiving a light signal input of a predetermined wavelength and producing an electrical signal proportion to the amount of light detected.

Figure 2D:
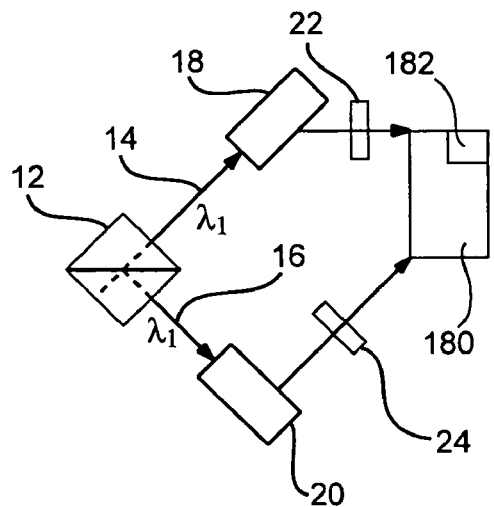

With reference to FIG. 2D, once first and second light beams (14 and 16) have been detected by first and second detectors (18 and 20) and electrical signals have been produced, those signals are transmitted to a signal processor for processing. In certain embodiments, each signal may be independently transmitted to signal processors 22 and 24 that may be configured to digitize the analog signals produced by the first and second detectors (e.g., 18 and 20) into data sets (e.g., first and second digital data sets). In certain embodiments, the first and second signal processors (22 and 24) may comprise an analog-to-digital converter (A/D converter) configured for independently sampling, digitizing and producing data.

As shown the first and second signal processors 22 and 24 are configured to be independent, however, they may also be configured to be part of a single processor 182 (e.g., a digital system processor), for instance within a computer processor unit (CPU) 180. First and second signal processors 22 and 24 may produce first and second data sets from the analog signals received from the first and second detectors (18 and 20), respectively. The data sets may be stored in memory and/or transmitted to a further component of the system, such as a processor 182, for further processing.

The system and method described above essentially produces, for each label employed in an array assay, two data sets. In certain embodiments, the data sets may be combined to produce a final data set that contains data that accurately reflects (i.e., describes) the actual amount of light emitted by the surface of the array as compared to either of the two data sets individually. As would be readily apparent to one of skill in the art, the data sets are combinable using a variety of methods. Embodiments illustrating several of many straightforward methods that could be employed are set forth below. In these embodiments, the data sets contain a numerical value representing the intensity of each pixel of a scan.

In one embodiment, the data set produced by the high sensitivity detector may be processed to identify pixels having values that are saturated (which value is 65,536 for a 16-bit scanner). Saturated values may be substituted by the values for the same pixel produced by the low sensitivity detector to produce the final data set.

In an alternative embodiment, the data set produced by the low sensitivity detector may be processed to identify pixels having values that are not significant from background. Such values may be substituted by the values for the same pixel produced by the high sensitivity detector to produce the final data set.

In a further embodiment, a processor may first identify data in either data set that is indicative of saturation and data that is indicative of being below the sensitivity of the given detector, and thereby determine useable data. Non-saturated signals may be detected because they are not at maximal magnitude. Additionally, signals indicating the presence of a detected label may be distinguished from background noise by virtue of the fact that the signal is above a set minimum point.

Once useable data has been determined the processor may then identify the useable data in each data set that refers to the same pixel and then compare the data referring to that pixel in the first set with the data referring to that same pixel in the second set. For example, the processor may compare individual data sets representing pixels derived from the outputs of the two detectors and select data in either set that is non-saturated, within the sensitivity of a given detector (i.e., the data is distinguishable from background noise), and has the highest relative magnitude (i.e., signal strength). In other words, if a plurality of data sets (e.g., from independent processors 22 and 24) of unsaturated input signals for a given pixel are detected, each set point for a given pixel from both data sets can be compared and the data that has the greatest overall magnitude for a given pixel may be selected to produce a numerical evaluation of the pixel which may then be output a single, integrated signal.

In another embodiment, each of the data sets may be subjected to feature extraction, to produce a numerical value for each feature. In the same manner as described above, values for saturated features produced by the high sensitivity detector may be substituted by the values for the same features produced by the low sensitivity detector to produce a final data set. Likewise, values for saturated features produced by the low sensitivity detector may be substituted by the values for the same features produced by the high sensitivity detector to produce a final data set.

It is to be noted, that although the system has been described with reference to detecting a single predetermined wavelength light (e.g., light from a single fluorescent label), one of ordinary skill in the art would readily be able to modify the system so as to detect pre-determined wavelengths of light, for example, "red" and "green" light emitted from fluorescent cyanine dyes that separately serve as an input light for two separate sets of first and second detectors.

Accordingly, in certain cases, a reader may contain two multi-detector systems, each system for detecting a different pre-determined wavelength of light. Pairs of compatible pre-determined wavelengths of light include, but are not limited to, those emitted by: Cy-3 and Cy-5 (Amersham Inc., Piscataway, N.J.), Quasar 570 and Quasar 670 (Biosearch Technology, Novato Calif.), Alexafluor555 and Alexafluor647 (Molecular Probes, Eugene, Oreg.), BODIPY V-1002 and BODIPY V1005 (Molecular Probes, Eugene, Oreg.), POPO-3 and TOTO-3 (Molecular Probes, Eugene, Oreg.), POPRO3 and TOPRO3 (Molecular Probes, Eugene, Oreg.), Pyrene, Coumarin, Diethylaminocoumarin, Fluorescein Chlorotriazinyl, Fluorescein, R110, Eosin, R6G, Tetramethylrhodamine, Lissamine, Napthofluorescein, Napthofluorescein, etc. Further suitable distinguishable detectable labels may be found in Kricka et al. (Ann Clin Biochem. 39:114-29, 2002). The wavelengths of the emissions of these labels are well known in the art.

In particular embodiments, the subject system may be used in conjunction with a dichroic beam splitter that splits light into two beams each containing a different pre-determined wavelength of light (one containing light emitted by one fluorescent label and the other containing light emitted by the other fluorescent label). Such a dichroic beam splitter, if employed, may be employed upstream from the current system within an array reader.

Turning now to FIG. 3, the system may further comprise a fiber coupling lens 32 which collects a portion of the laser-induced fluorescence (LIF) from the array, an optical fiber 34, a collimating lens 36, and a filter 26. These components may be configured relative to one another in any way so long as they are configured for receiving light emitted from an area on a chemical array and transmitting that light. For instance, any suitable fiber may be used, such as an optical fiber, which may be either a single or multi-mode optical fiber. Additionally, any type of filter may be used so long as it is adapted for receiving light from one source and passing the light of the appropriate wavelength while at the same time filtering out light of inappropriate wavelengths, such as light at the wavelength supplied by an excitatory laser.

Accordingly, as seen in FIG. 3, an array reader 2 with a wide dynamic range detection system of a representative embodiment of the subject invention is provided. The wide dynamic range detector system is configured for detecting light of a predetermined wavelength 8 and may include any and/or all of: (a) a multimode optical fiber 34, configured for receiving light of a predetermined wavelength 8 emitted from an area of a chemical array and transmitting that light to a receiving element; (b) a collimating lens 36 that is adapted for receiving light from a transmitting element (e.g., an optical fiber) and is configured for producing a collimated light beam that may be transmitted through a filter and to a beam splitter; (c) a filter 26 that is configured to reduce transmission of light that is not at the pre-determined wavelength; (d) a beam splitter 12 configured to split the light of a predetermined wavelength 8 into a first light beam 14 and a second light beam 16, wherein each of the beams is at the pre-determined wavelength of light; (e) a first detector 18 for detecting photons in the first light beam 14; and (f) a second detector 20 for detecting photons in the second light beam 16. Additionally, the wide dynamic range detection system 10 may be adapted to be part of an array reader 2 that may include both a laser excitation system 100 that is configured to illuminate an area on a surface of a polymeric array, and a data processing system that is configured for processing signals produced by the first and second detectors. The processing system may be part of a computer processing unit that may be configured for further processing and/or storing the data.

Depending on how the system is configured, other system components may be present in the system, such as a plurality of converters, for converting an analog signal to a digital signal (e.g., such as A/D converters); a current-to-voltage; voltage-to-current integrator; signal amplifiers; or other processors; and the like. For instance, in one embodiment, the dual detection hardware could be comprised of a monolithic assembly.

Figure 4:
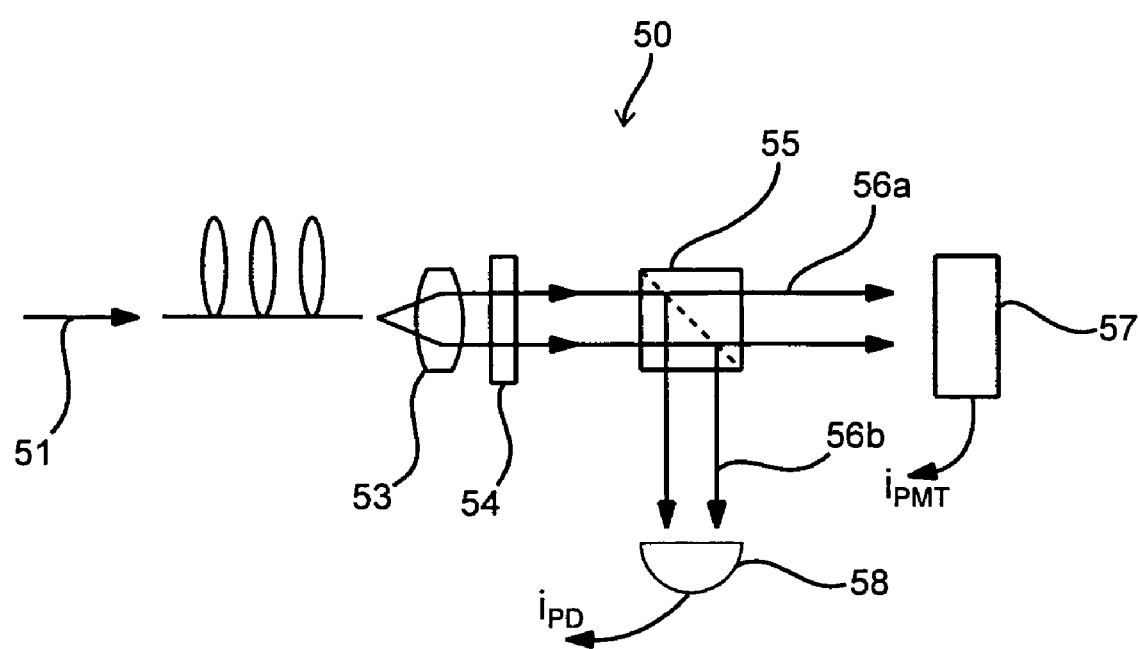
FIG. 4 schematically illustrates an embodiment of a monolithic system of the present invention, wherein all the components of the system are fixed and therefore do not move in relation to one another.

FIG. 4 provides a representative view of such a monolithic assembly. In the embodiment depicted in FIG. 4, assembly 50 includes a multimode (MM) fiber 52 configured to accept laser induced fluorescence (LIF) 51 from a scanner. Light exiting MM fiber 52 passes through collimating lens 53, filter 54, and beam splitter 55, to produce two beams of light 56a and 56b. As shown, light beam 56a is detected by PMT detector 57 while light beam 56b is detected by Si-PD 58. A feature of the assembly 50 shown in FIG. 4 is that the assembly is configured so that the individual components may not move in relation to one another, and therefore the system allows zero degrees freedom of movement when subjected to various environmental stimuli (temperature, vibration, humidity, etc.). Such an assembly would remain aligned and could be inserted into an existing reader, so as to retrofit and upgrade the existing reader.

In addition to the system described above, the invention provides a method for detecting light emitted from an area on a surface of a biopolymer array, that may include any combination or all of the following: collimating the light; filtering the light; splitting it into a first light beam and second light beam; detecting photons in said first light beam with a first detector; and detecting photons in said second light beam with a second detector. Additionally, the amplitudes of the light signals detected by the first and second detectors are converted into signals that are transmitted to a processor where they are processed to produce data that may be stored.

The invention also provides a variety of computer-related embodiments. Specifically, the methods described may be executed by a processor in accordance with instructions from a computer program product. Accordingly, the invention provides a processor programmed to input multiple digital signals for a pixel, process these signals to identify a non-saturated input signal, and output data corresponding to that single non-saturated input signal that is an integrated read out of the wide dynamic range reader of the subject invention, as discussed above. Additionally, the two signals from the first and second detectors could not only be combined into one image of increased dynamic range, but could also be output as two separate images, each covering a different range of intensity values. Also, if desired, a quick pre-scan could be implemented to identify high intensity features using the low-gain/sensitivity detector, which could then be used to set the parameters of both the low sensitivity and high sensitivity detectors and the over all system.

In certain embodiments, the above methods are coded onto a computer-readable medium in the form of "programming" or "programming products" as instructions, where the term "computer readable medium" as used herein refers to any storage or transmission medium that participates in providing instructions and/or data to a computer for execution and/or processing. Examples of storage media include floppy disks, magnetic tape, CD-ROM, a hard disk drive, a ROM or integrated circuit, a magneto-optical disk, or a computer readable card such as a PCMCIA card and the like, whether or not such devices are internal or external to the computer. A file containing information may be "stored" on computer readable medium, where "storing" means recording information such that it is accessible and retrievable at a later date by a computer. Therefore, the computer program product comprises programming coded onto computer-readable medium, and the programming and the processor may be part of a computer-based system.

With respect to computer readable media, "permanent memory" refers to memory that is permanent. Permanent memory is not erased by termination of the electrical supply to a computer or processor. Computer hard-drive ROM (i.e. ROM not used as virtual memory), CD-ROM, floppy disk and DVD are all examples of permanent memory. Random Access Memory (RAM) is an example of non-permanent memory. A file in permanent memory may be editable and re-writable.

A "computer-based system" refers to the hardware means, software means, and data storage means used to analyze the information of the present invention. The minimum hardware of the computer-based systems of the present invention comprises a central processing unit (CPU), input means, output means, and data storage means. A skilled artisan can readily appreciate that any one of the currently available computer-based system are suitable for use in the present invention. The data storage means may comprise any manufacture comprising a recording of the present information as described above, or a memory access means that can access such a manufacture.

To "record" data, programming, or other information on a computer readable medium refers to a process for storing information, using any such methods as known in the art. Any convenient data storage structure may be chosen, based on the means used to access the stored information. A variety of data processor programs and formats can be used for storage, e.g. word processing text file, database format, etc.

The subject systems and methods find particular use in chemical array readers. Accordingly, also provided by the subject invention is an array reader that contains a system for performing the subject methods described above. Typically, such readers have a laser excitation system for emitting light from the surface of an array, hardware for performing the methods described above, and, usually, a storage medium for storing data produced by scanning. A reader may also contain or communicate with a processor including programming for executing the subject methods. Since array readers typically measure at least two, and sometimes three, four or five or more wavelengths of light from the surface of an array, a subject reader may have a corresponding number (e.g., 2, 3, 4, 5, or more) systems for performing the subject methods. In many embodiments, a subject reader will typically contain at least two such systems, corresponding to the "red" and "green" channels of light emitted in typical array experiments (Cheung et al., Nature Genetics 1999, 21: 15-19).

Any optical reader or device may be provided to include the above programming. Representative optical readers of interest include those described in U.S. Pat. Nos. 5,585,639;

5,760,951; 5,763,870; 6,084,991; 6,222,664; 6,284,465; 6,329,196; 6,371,370 and 6,406,849—the disclosures of which are herein incorporated by reference. An exemplary optical reader as may be used in the present invention is shown in FIG. 5.

Figure 5:
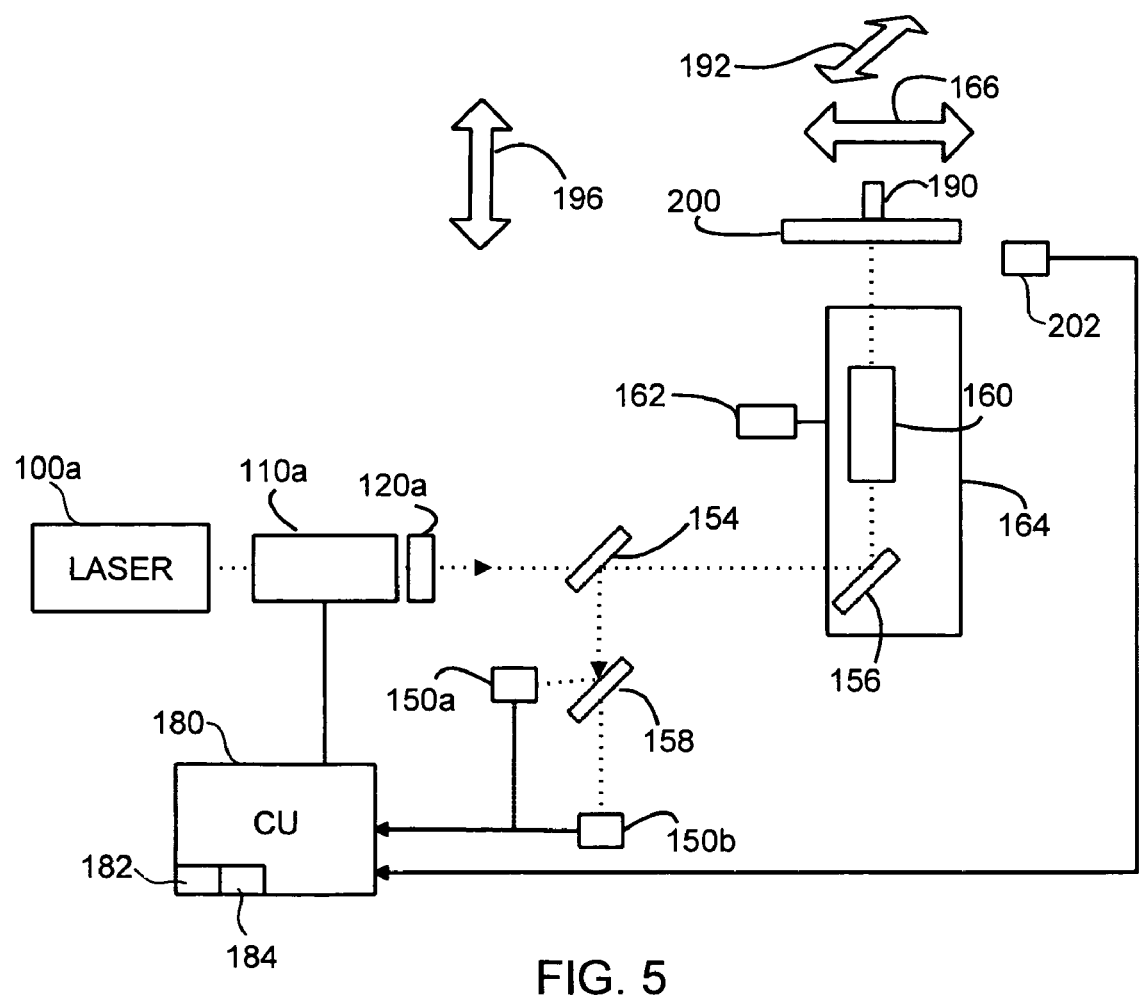
FIG. 5 schematically illustrates an embodiment of an optical reader system of the present invention.

Referring now to FIG. 5, an exemplary apparatus of the present invention (which may be generally referenced as an "array reader") is illustrated. A light system provides light from laser 100a which can be regulated to control the optical power arriving at the array. In this schematic illustration in FIG. 5, the laser is regulated via an external electro-optic modulator (EOM) 110a with attached polarizer 120a. A second laser (not shown) may be included, wherein each laser would emit a different wavelength of light (e.g., one providing red light and the other green light) and each would have its own corresponding EOM and polarizer. A control signal in the form of a variable voltage applied to the EOM 110a by the controller (CU) 180, changes the polarization of the exiting light which is thus more or less attenuated by the corresponding polarizer 120a. Controller 180 may be or include a suitably programmed processor.

Thus, the EOM 110a and corresponding polarizer 120a together act as a variable optical attenuator which can alter the power of an interrogating light spot exiting from the attenuator. This function can also be performed using any number of variable attenuators, including liquid crystal-based modulators and variable neutral density filters. Alternatively, some lasers can be modulated directly, via analog control signals. The remainder of the light from laser 100a is transmitted through a dichroic beam splitter 154, reflected off fully reflecting mirror 156 and focused onto an array mounted on holder 200, using optical components in beam focuser 160. Light emitted (in particular, fluorescence) at a predetermined wavelength (e.g., green or red light) from features on the array, in response to the interrogating light, is imaged using the same optics in focuser/scanner 160, and is reflected off a mirror 156 and dichroic beamsplitter 154.

The predetermined wavelength of light (e.g., green or red) will then be split by beam splitter 158 into a first and second light beam each of the particular wavelength (e.g., green or red), and then be detected by first and second detectors (e.g., 150a, 150b). More optical components (not shown) may be used between the dichroic beam splitter 154 and the achromatic beam splitter 158 (such as a collimating lens or a filter) and between non-chromatic beam splitter 158 and each detector 150a, 150b (such as lenses, pinholes, filters, fibers, etc.).

All of the optical components through which light emitted from an array or calibration member in response to the illuminating laser light, passes to detectors 150a and 150b, together with those detectors, form a detection system. This detection system has a fixed focal plane. A scan system causes the illuminating region in the form of a light spot from a laser 100a and a detecting region of each detector 150a, 150b (which detecting region will form a pixel in the detected image), to be scanned across multiple regions of an array or array package mounted on holder 200. The scanned regions for an array will include at least the multiple features of the array. In particular the scanning system is typically a line by line scanner, scanning the interrogating light in a line across an array when at the reading position, in a direction of arrow 166, then moving ("transitioning") the interrogating light in a direction into/out of the paper as viewed in FIG. 5 to a position at an end of a next line, and repeating the line scanning and transitioning until the entire array has been scanned.

This scanning feature is accomplished by providing a housing containing mirror 156 and focuser 160, which housing can be moved along a line of pixels (i.e., from left to right or the reverse as viewed in FIG. 5) by a transporter 162. The second direction 192 of scanning (line transitioning) can be provided by second transporter which may include a motor and belt (not shown) to move caddy 200 along one or more tracks. The second transporter may use a same or different actuator components to accomplish coarse (a larger number of lines) movement and finer movement (a smaller number of lines). Generally, directly adjacent rows are scanned. However, "adjacent" rows may include alternating rows or rows where more than one intervening row is skipped.

The optical reader of FIG. 5 may further include a reader (not shown) which reads an identifier from an array package. When identifier is in the form of a bar code, that reader may be a suitable bar code reader.

Of course, the movements 166 and 192 may be accomplished by actuating holder 200 or housing alone. Still further, the movement roles described for each element above may be swapped.

The system may also include detector 202, processor 180, and a motorized or servo-controlled adjuster 190 to move holder 200 in the direction of arrow 196 to establish correct focus for the system. In addition, such an autofocus system may contain a position detector e.g. a quadrature position encoder, also feeding back to the CU measures the absolute position (i.e., relative to the apparatus) of the servo-controlled adjuster 190. As above with respect to movements 166 and 192, it should be observed that focus servo control movement 196 may occur in connection with housing 164 instead of the holder, or, if the detection system is not a fixed focal plane system, by an adjustment of laser focuser 160. Further details regarding suitable chemical array autofocus hardware is described in U.S. Pat. No. 6,486,457, as well as European publication EP 1091229 published Apr. 11, 2001.

Controller 180 of the apparatus is connected to receive signals from detectors 150a, 150b that are signals which result from the detection of the predetermined wavelength from emitted light for each scanned region of an array when at the reading position mounted in holder 200. Controller 180 also receives the signal from autofocus detector 202, which is used to control the scan system. Controller 180 contains all the necessary software to detect signals from detector 150a, 150b and regulate a motorized or servo-controlled adjuster 190 through a control loop. Controller 180 may also analyze, store, and/or output data relating to emitted signals received from detectors 150a, 150b in a known manner.

Controller 180 also includes a programmable digital signal processor for performing the methods described above, and usually includes plurality of analog-to-digital converters, and other components of a multi-detector detection system (such as a multi-detector photodetection system), e.g., a current-to-voltage converter, voltage amplifier, etc., as desired, a media reader 182 which can read a portable removable media (such as a magnetic or optical disk), and a communication module 184 which can communicate over a communication channel (such as a network, for example the internet or a telephone network) with a remote site (such as a database at which information relating to array package may be stored in association with the identification).

In one mode of operation, an array in a package is typically first exposed to a liquid sample. This liquid sample may be placed directly on the array or introduced into a chamber through a septa in the housing of the array. After a time to allow, for example, hybridization, the array may then be washed and scanned with a liquid (such as a buffer solution) present in the chamber and in contact with the array, or it may be dried following washing. After mounting a given array in cradle 200 (either with the array features on the glass surface nearer to, or further from, the lens—depending, at least, upon the lens setup) the identifier reader may automatically (or upon operator command) read an identifier from the array package, which may be used to e.g. retrieve information on the array layout from a database containing the identifier in association with such information. Such a database may be a local database accessible by controller 180 (such as may be contained in a portable storage medium in drive 182.

The saved results from a sample exposed array, read with the methods described above, may be raw results (such as fluorescence intensity readings for each feature in one or more color channels) or may be processed results such as obtained by rejecting a reading for a feature which is below a predetermined threshold and/or forming conclusions based on the pattern read from the array (such as whether or not a particular target sequence may have been present in the sample). The results of the reading (processed or not) may be forwarded (such as by communication of data representing the results) to a remote location if desired, and received there for further use (such as further processing).

The subject array readers find use in a variety applications, where such applications are generally analyte detection applications in which the presence of a particular analyte in a given sample is detected at least qualitatively, if not quantitatively. Protocols for carrying out array assays are well known to those of skill in the art and need not be described in great detail here. Generally, the sample suspected of comprising the analyte of interest is contacted with an array under conditions sufficient for the analyte to bind to its respective binding pair member that may be present on the array.

Thus, if the analyte of interest is present in the sample, it binds to the array at the site of its complementary binding member and a complex is formed on the array surface. The presence of this binding complex on the array surface is then detected, e.g., through use of a signal production system such as a fluorescent label present on the analyte, etc, where detection includes scanning with an optical reader according to the present invention. The presence of the analyte in the sample is then deduced from the detection of binding complexes on the substrate surface.

Specific analyte detection applications of interest include hybridization assays in which the nucleic acid arrays of the subject invention are employed. In these assays, a sample of target nucleic acids is first prepared, where preparation may include labeling of the target nucleic acids with a label, e.g., a member of signal producing system. Following sample preparation, the sample is contacted with the array under hybridization conditions, whereby complexes are formed between target nucleic acids that are complementary to probe sequences attached to the array surface. The presence of hybridized complexes is then detected. Specific hybridization assays of interest which may be practiced using the subject arrays include: gene discovery assays, differential gene expression analysis assays; nucleic acid sequencing assays, comparative genomic hybridization (CGH) applications, localization applications, and the like. References describing methods of using arrays in various applications include U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992—the disclosures of which are herein incorporated by reference.

Where the arrays are arrays of polypeptide binding agents, e.g., protein arrays, specific applications of interest include analyte detection/proteomics applications, including those described in U.S. Pat. Nos. 4,591,570; 5,171,695; 5,436,170; 5,486,452; 5,532,128 and 6,197,599 as well as published PCT application Nos. WO 99/39210; WO 00/04832; WO 00/04389; WO 00/04390; WO 00/54046; WO 00/63701; WO 01/14425 and WO 01/40803—the disclosures of which are herein incorporated by reference.

In using an array in connection with a reader according to the present invention, the array will typically be exposed to a sample (such as a fluorescently labeled analyte, e.g., protein containing sample) and the array then read. Reading of the array may be accomplished by illuminating the array and reading the location and intensity of resulting fluorescence at each feature of the array to detect any binding complexes on the surface of the array. Certain embodiments of the invention may involve transmitting data obtained from a method described above from a first location to a remote location. Certain other embodiments of the invention may involve receiving, from a remote location, data obtained from a method described above.

In reading the array, pixel signals are usually processed using the methods described above.

It is further noted that aspects of the invention may be applicable to a variety of optical readers, e.g., scanners, including those that detect chemiluminescent or electroluminescent labels. The present invention will be applicable to such readers where powering down the reader will result in lifetime savings, as exemplified above.

Kits for use in connection with the subject invention may also be provided. In one embodiment, a kit of the subject invention may include a system for detecting light of a predetermined wavelength emitted from an area on a surface of a chemical array. The system of representative embodiments includes at least a first and a second detector for detecting photons in a single light beam of a particular wavelength of light emitted from the array. Accordingly, the kit will include at least a first and a second detector. In one embodiment, the system may additionally include a beam splitter that is configured to split light into a first light beam and a second light beam, each of which are at the same pre-determined wavelength. In this embodiment, the kit will include at least a beam splitter and first and second detectors for detecting photons in said first and second light beams, respectively. Additionally, the kit may include one or more of the following: an optical fiber (e.g., a multi-mode optical fiber), a filter configured to reduce transmission of background light, and a collimating lens adapted for producing a collimated light beam, all of which are in light transmitting relationship with one another.

Accordingly, in a further embodiment, a kit for upgrading an existing reader having the system components of the invention is provided. For instance, a suitable kit may contain one or more beam splitters and a plurality of detectors (e.g., first and second detectors). Further components that may be included in such a kit are one or more fibers (e.g., optical fibers), collimating lenses, and/or filters, as described above, that may be used to retrofit an existing optical reader. In one embodiment, the kit includes a monolithic assembly consisting of a fiber connector (to accept a multimode fiber), collimating lens, filter, beam splitter, and a Si-PD and/or a PMT, wherein the assembly is configured so that the individual components may not move in relation to one another, and therefore the system allows zero degrees freedom of movement when subjected to various environmental stimuli (temperature, vibration, humidity, etc.). Such an assembly is configured to remain aligned and is to be inserted into an existing reader, so as to retrofit and upgrade the existing reader.

Additionally, kits of the subject invention usually include at least a computer program product comprising computer readable medium including programming as discussed above and, in certain kits, instructions. The instructions may include installation or setup directions. The instructions may include directions for use of the invention with options or combinations of options as described above. In certain embodiments, the instructions include both types of information.

Providing the software and instructions as a kit may serve a number of purposes. The combination may be packaged and purchased as a means of upgrading an existing reader. Alternately, the combination may be provided in connection with a new reader in which the software is preloaded on the same. In which case, the instructions will serve as a reference manual (or a part thereof) and the computer readable medium as a backup copy to the preloaded utility.

The instructions are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging), etc. In other embodiments, the instructions are present as an electronic storage data file present on a suitable computer readable storage medium, e.g., CD-ROM, diskette, etc, including the same medium on which the program is presented.

In yet other embodiments, the instructions are not themselves present in the kit, but means for obtaining the instructions from a remote source, e.g., via the Internet, are provided. An example of this embodiment is a kit that includes a web address where the instructions can be viewed and/or from which the instructions can be downloaded. Conversely, means may be provided for obtaining the subject programming from a remote source, such as by providing a web address. Still further, the kit may be one in which both the instructions and software are obtained or downloaded from a remote source, as in the Internet or world wide web. Some form of access security or identification protocol may be used to limit access to those entitled to use the invention. As with the instructions, the means for obtaining the instructions and/or programming is generally recorded on a suitable recording medium.

In addition to the subject programming and instructions, the kits may also include one or more reference arrays, e.g., two or more reference arrays for use in testing an optical reader after software installation.

EXAMPLES

The following examples are put forth so as to provide those of ordinary skill in the art with a complete disclosure and description of how to make and use the present invention, and are not intended to limit the scope of what the inventors regard as their invention. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

The following illustrates that by using the teachings of the subject invention the dynamic range of an array reader can be increased at least about 10 fold, at least about 100 fold, and at least about 1000-fold. In the present example, an Agilent Technologies, Inc. G2505B Reader was modified so as to increase it's over all dynamic range. Instead of using an array reader with only one detector, the reader was modified, in accordance with the teachings above, to include a second detector. Instead of using a beam splitter two consecutive scans were taken of a Cy-dye calibration chip, from Full Moon Biosystems, Inc.), and then compared. One scan was taken using the G2505B Reader in a standard configuration, but with the PMT gain set at 10%. A second scan was taken by routing the reader optical fibers (one at a time) to a Si-PD and ultimately, to an oscilloscope to read the LIF signal via the Si-PD detector. A scan image of the FMB chip is shown and described in FIG. 6.

Figure 6:
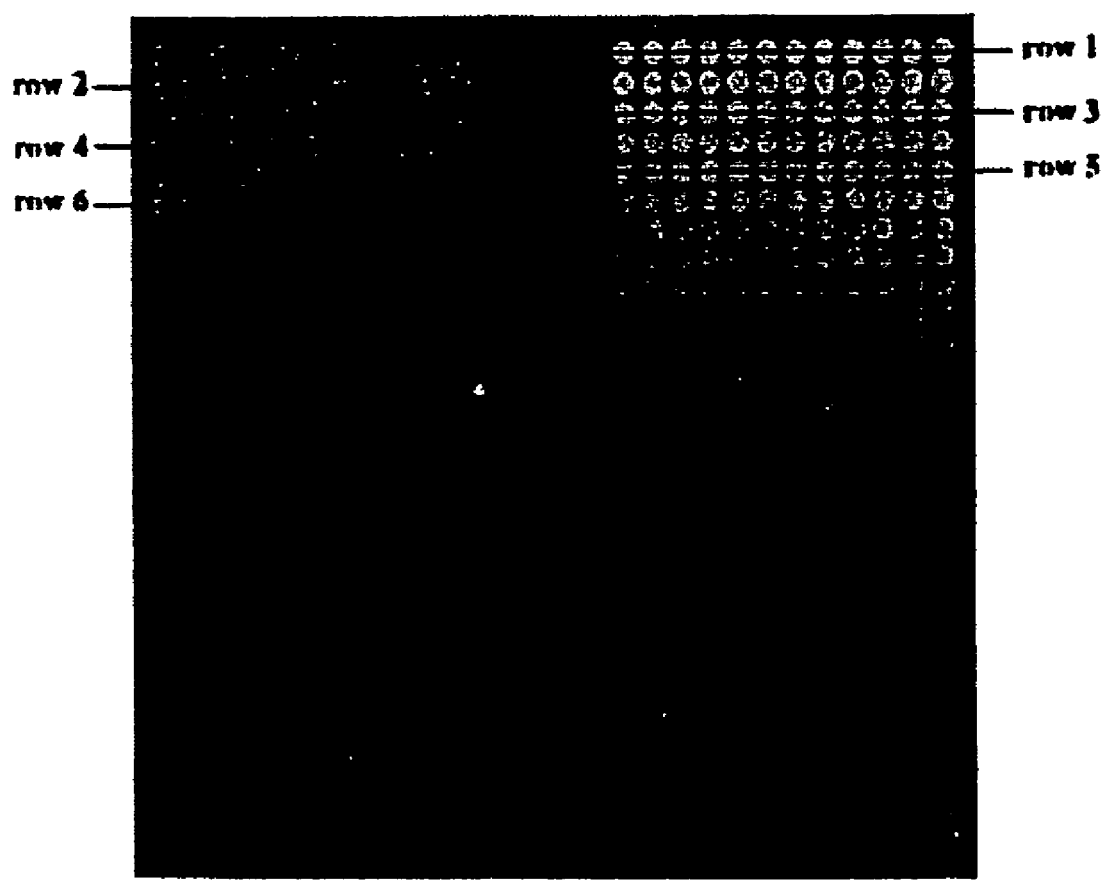
FIG. 6 is a scan image of a calibration chip that compares two consecutive scans of the chip with two different detectors.

FIG. 6 is a scan image of the Full Moon Biosystems, Inc. calibration chip. The group of green spots on the left side of the image contain Cy3 dye, while the group of red spots on the right side contains Cy5 dye. In each group, the Cy-dye concentration varies from top to bottom, the top being the most concentrated and thus, the brightest features. Each group contains 12 columns where for a given row, the Cy-dye concentration remains constant across the columns. The highlighted rows are cuts analyzed in turn by both the PMT and the Si-PD detectors (see FIGS. 7A and 7B). The uppermost rows are fully saturated in the G2505B Reader at 100% PMT gain setting—the default scanning setting that obtains the highest sensitivity.

Figure 7A:
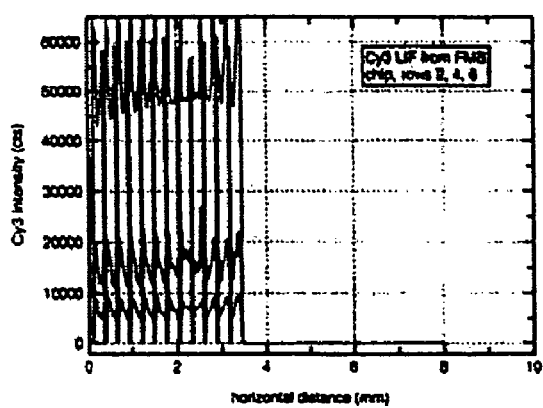
FIGS. 7A-7B provide a comparison of scan signals derived from two consecutive scans of a calibration chip with two different detectors.
Figure 7B:
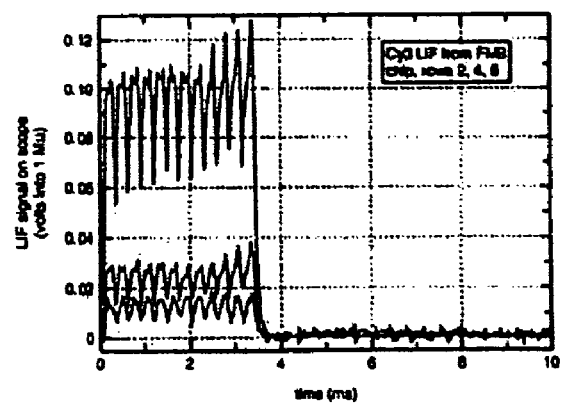
Figure 8A:
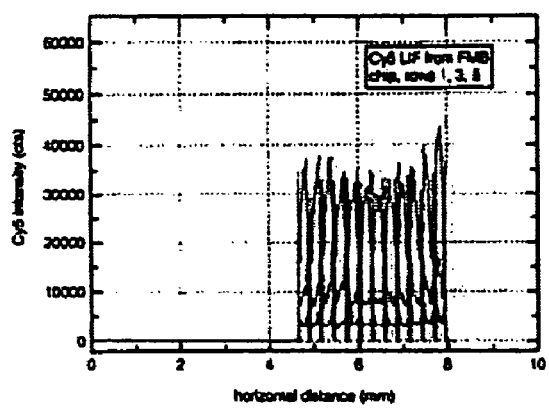
FIGS. 8A-8B are a comparison of scan signals derived from two consecutive scans of a calibration chip with two different detectors.
Figure 8B:
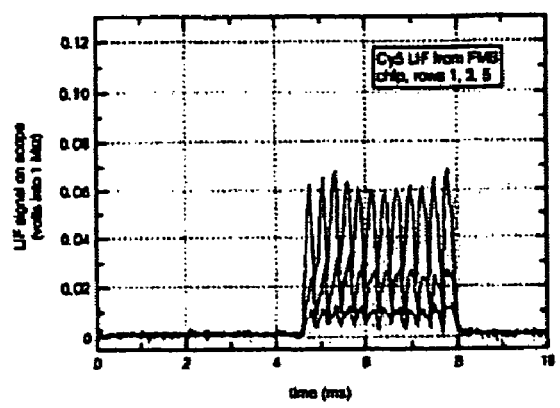

FIGS. 7A-B and 8A-B show side-by-side comparisons of scans taken in turn on the modified reader. FIGS. 7A and 7B are a comparison of scan signals derived from rows 2, 4, 6 of the FMB chip, on the left hand side of the array, i.e., the side containing Cy3 dye. The left graph (FIG. 7A) is taken from the reader with a PMT gain setting of just 10%, while the right graph (FIG. 7B) is the signal derived from a less sensitive detector (e.g., a Si-PD). FIGS. 8A and 8B are a comparison of scan signals derived from rows 1, 3, 5 of the FMB chip, on the left hand side of the array, i.e., the side containing Cy5 dye. The left graph (FIG. 8A) is taken from the reader with a PMT gain setting of just 10%, while the right graph (FIG. 8D) is the signal derived from a less sensitive detector (e.g., a Si-PD).

The scan data plotted on the left were extracted from scans on the G2505B Reader with the PMT gain set to only 10%, while the data plotted on the right was recorded on an oscilloscope after routing the appropriate fiber optic cable from the reader to a Newport 818-UV Si-PD (via the Newport 818FA fiber adapter) and Newport 1835 Power Meter. The analog output of the 1835 Power Meter was sent to an Agilent infiniium scope set at 1 MΩ input impedance. Comparison of left and right graphs shows that even with this non-optimized system, the Si-PD is faithfully reproducing the signals detected by the gain-reduced PMT. This experiment thus demonstrates at least a 10-fold increase in dynamic range, which can be increased at least about 100 fold, and at least about 1000-fold more dependent on what components are used and how they are configured.

All publications and patents cited in this specification are herein incorporated by reference as if each individual publication or patent were specifically and individually indicated to be incorporated by reference. The citation of any publication is for its disclosure prior to the filing date and should not be construed as an admission that the present invention is not entitled to antedate such publication by virtue of prior invention.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present inven-

What is claimed is:

1. A system for detecting light of a pre-determined wavelength range emitted from an area on a surface of a chemical array, said system comprising:
   a) a beam splitter configured to split said light into a first light beam and a second light beam;
   b) a first detector for detecting photons in said first light beam; and
   c) a second detector for detecting photons in said second light beam; wherein said first and second detectors are different types of detectors, wherein said first and second detectors are different types of detectors configured to detect light emitted from an area on a surface of a chemical array, wherein said first and second detectors have an overlapping dynamic range.

2. The system of claim 1, wherein said beam splitter is an achromatic beam splitter.

3. The system according to claim 1, wherein said first detector is configured to detect lower intensity light than said second detector.

4. The system according to claim 1, wherein said chemical array is a polynucleotide array or a polypeptide array.

5. The system according to claim 1, wherein said first detector is more sensitive than said second detector.

6. The system according to claim 1, wherein said first and second detectors comprise detectors that are selected from the group consisting of: a photo-multiplier tube (PMT), a photo-diode (PD), an avalanche photodiode (APD), a charge-coupled device (CCD), a charge-injection device (CID), and a complementary-metal-oxide-semiconductor detector (CMOS) device.

7. The system according to claim 1, wherein one of said first or second detectors comprises a photo-multiplier tube (PMT).

8. The system according to claim 1, wherein one of said first or second detectors comprises a photo-diode (PD).

9. The system according to claim 8, wherein said photo-diode (PD) comprises a silicon photo-diode (Si-PD).

10. The system according to claim 1, wherein said first detector is a PMT and said second detector is an Si-PD.

11. The system according to claim 1, further comprising a collimating lens for producing a collimated light beam that is transmitted toward said beam splitter.

12. The system according to claim 11, further comprising a multi-mode optical fiber for receiving said light emitted from said area and transmitting said light to said collimating lens.

13. The system according to claim 1, further comprising a filter for reducing transmission of light that is not at said pre-determined wavelength.

14. The system according to claim 13, wherein said filter is positioned or positionable to receive light from a collimating lens and pass said light to said beam splitter.

15. The system according to claim 1, wherein the system is configured to form a structure, wherein all the elements are fixed in position relative to one another.

16. A system for detecting light of a pre-determined wavelength range emitted from an area on a surface of a chemical array, said system comprising:
   a) a filter to reduce transmission of light that is not at a pre-determined wavelength range;
   b) a collimating lens for producing a collimated light beam that is transmitted toward a beam splitter;
   c) a beam splitter to split said light into a first light beam and a second light beam, each of said beams comprising said pre-determined wavelength range of light;
   d) a first detector for detecting photons in said first light beam; and
   e) a second detector for detecting photons in said second light beam wherein said first and second detectors are different types of detectors, wherein said first and second detectors are different types of detectors configured to detect light emitted from an area on a surface of a chemical array, wherein said first and second detectors have an overlapping dynamic range.

17. The system according to claim 16, wherein the first detector is a PMT.

18. The system according to claim 16, wherein the first detector is a Si-PD.

19. The system according to claim 16, wherein the system is configured to form a structure, wherein all the elements are in a fixed position relative to one another.

20. An array reader, comprising: a) a laser excitation system configured to illuminate an area on a surface of a chemical array; and b) a system for detecting light according to claim 16.

21. The array reader according to claim 20, wherein said system further comprises a data processing system configured for processing signals produced by said first and second detectors.

22. The array reader according to claim 20, further comprising a storage medium configured for storing processed data.

23. The array reader according to claim 22, wherein said storage medium is a computer memory.

24. The array reader according to claim 20, wherein said processing system outputs a data signal where the dynamic range read is from 1 to 1.times.10.sup.8.

25. The array reader according to claim 23, wherein said data signal is a single integrated data signal.

26. A method for assaying a sample within a chemical array, said method comprising: a) contacting a chemical array with a sample; and b) reading said array with an array reader according to claim 20.

27. The method of claim 26, further comprising storing said data on a computer-readable medium.

28. The method of claim 27, wherein said computer-readable medium is a computer memory.

29. The method of claim 26, wherein said array is a polynucleotide array.

30. The method of claim 26, wherein said array is a polypeptide array.

31. A method for detecting a pre-determined wavelength of light emitted from an area on a surface of a chemical array, said method comprising:
   a) splitting said light into a first light beam and second light beam, each comprising said pre-determined wavelength of light;
   b) detecting photons in said first light beam with a first detector; and
   c) detecting photons in said second light beam with a second detector; wherein said first and second detectors are different types of detectors to detect light emitted from an area on a surface of a chemical array, wherein said first and second detectors have an overlapping dynamic range, and wherein said chemical array is a polynucleotide array or a polypeptide array.

32. The method according to claim 31, further comprising collimating said light prior to said splitting.

33. The method according to claim 32, further comprising processing signals from said first and second detectors to produce data.

34. The method according to claim 32, further comprising storing said data.

35. A system for detecting light of a pre-determined wavelength range emitted from an area on a surface of a chemical array, said system comprising:
 a) a beam splitter configured to split said light into a first light beam and a second light beam;
 b) a first detector for detecting photons in said first light beam; and
 c) a second detector for detecting photons in said second light beam; wherein said first and second detectors are different types of detectors,
 d) a collimating lens for producing a collimated light beam that is transmitted toward said beam splitter, and
 e) a multimode optical fiber for receiving said light emitted from said area and transmitting said light to said collimating lens, wherein said first and second detectors are different types of detectors to detect light emitted from an area on a surface of a chemical array.

* * * * *